(12) United States Patent
Lundin

(10) Patent No.: US 11,401,308 B2
(45) Date of Patent: Aug. 2, 2022

(54) PEPTIDES AND THEIR USE IN DIAGNOSIS

(71) Applicant: Biotome Pty Ltd., West Perth (AU)

(72) Inventor: Bror Samuel Lundin, Mölndal (SE)

(73) Assignee: Biotome Pty Ltd., West Perth (AU)

( * ) Notice: Subject to any disclaimer, the term of this patent is extended or adjusted under 35 U.S.C. 154(b) by 0 days.

(21) Appl. No.: 16/488,077

(22) PCT Filed: Feb. 22, 2018

(86) PCT No.: PCT/EP2018/054396
§ 371 (c)(1),
(2) Date: Aug. 22, 2019

(87) PCT Pub. No.: WO2018/153991
PCT Pub. Date: Aug. 30, 2018

(65) Prior Publication Data
US 2020/0062806 A1  Feb. 27, 2020

(30) Foreign Application Priority Data

Feb. 24, 2017 (SE) .................................. 1750203-0

(51) Int. Cl.
C07K 14/205 (2006.01)
G01N 33/569 (2006.01)
G01N 33/574 (2006.01)

(52) U.S. Cl.
CPC ..... *C07K 14/205* (2013.01); *G01N 33/56922* (2013.01); *G01N 33/57446* (2013.01); *G01N 2333/205* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 6,019,974 A | 2/2000 | L'Hernault | |
| 6,902,903 B1 | 6/2005 | Quan et al. | |
| 7,141,244 B1 * | 11/2006 | Covacci | A61K 39/105 |
| | | | 424/234.1 |
| 2005/0014138 A1 | 1/2005 | Rath | |
| 2005/0260581 A1 * | 11/2005 | Fontana | A61P 35/00 |
| | | | 435/6.15 |
| 2015/0153356 A1 * | 6/2015 | Meng | C07K 16/2866 |
| | | | 506/9 |
| 2016/0030510 A1 | 2/2016 | Lu et al. | |

FOREIGN PATENT DOCUMENTS

| | | |
|---|---|---|
| CN | 1313337 A | 9/2001 |
| CN | 104147589 A | 11/2014 |
| JP | 2000350591 A | 12/2000 |
| JP | 2004123737 A | 4/2004 |
| JP | 200655168 A | 3/2006 |
| WO | 2001/042277 A2 | 6/2001 |
| WO | 2016/172722 A1 | 10/2016 |

OTHER PUBLICATIONS

Yasuda, A. et al., A novel diagnostic monoclonal anibody specific for Helicobacter pylori CagA of East Asian type, APMIS, 117(12): 893-899, Nov. 17, 2009.
Gholi, M, et al., Helicobacter pylori FliD protein is a highly sensitive and specific marker for serologic diagnosis of H. pyrlori infection, International Journal of Medical Microbiology, 303(8): 618-623, Dec. 8, 2013.
English translation of Notice of Reasons for Refusal for Japanese Patent Application No. 2019-567783, dated Nov. 16, 2021.

* cited by examiner

*Primary Examiner* — Oluwatosin A Ogunbiyi
(74) *Attorney, Agent, or Firm* — Julie K. Staple; Dinsmore & Shohl LLP

(57) ABSTRACT

There is provided novel peptides for use in diagnosis of CagA+ *H. pylori* infection or the prediction of risk for gastric cancer. The peptides bind antibodies from CagA+ *H. pylori* patients with high specificity and sensitivity, and can be used for example in a diagnostic kit.

8 Claims, 4 Drawing Sheets
Specification includes a Sequence Listing.

PEPTIDES AND THEIR USE IN DIAGNOSIS

FIELD OF THE INVENTION

This invention relates to novel peptides from the CagA protein of *Helicobacter pylori*. The peptides can be used for improved prevention, diagnosis and treatment of bacterial infection and assessment of gastric cancer risk.

SEQUENCE LISTING

The instant application contains a Sequence Listing which has been submitted electronically as a file in ASCII format and is hereby incorporated by reference in its entirety. Said ASCII format file, created on Jan. 24, 2022, is named 47BIOT-NO10102PA.txt and is 67,540 bytes in size.

BACKGROUND

*Helicobacter pylori* is a bacterium usually found in the stomach. Some *H. pylori* strains carry the CagA (cytotoxicity-associated antigen A) gene which encodes for a virulence factor. The CagA gene encodes the 1140 to 1180-amino acid protein CagA which is a bacterial oncoprotein that is translocated into stomach epithelial cells at the site of infection. Upon translocation, it affects intracellular signalling pathways of the epithelial cell.

*H. pylori* bacteria carrying the CagA gene are associated with increased risk for gastric cancer development, and presence of anti-CagA-antibodies is associated with increased future gastric cancer risk. Early detection of CagA+ *H. pylori* infection can lead to increased cancer survival, as eradication of infection in infected individuals reduces gastric cancer risk. Therefore, a method that identifies individuals carrying CagA+ *H. pylori* can be used to diagnose high gastric cancer risk, and thereby assist prevention of gastric cancer development.

However, existing serology methods for CagA+ *H. pylori* infections are not clinically useful, mainly because they are not specific enough. There are high levels of false-positive samples indicating widespread antibody reactivity to CagA even in individuals not infected with *H. pylori*, or in individuals infected with a *H. pylori* strain lacking CagA. Thus, specificity and sensitivity has not been sufficient for a clinically useful diagnostic test (Yamaoka et al, J Clin Microbiol 1998:36:3433; Yamaoka et al, Gastroenterology 1999:117:745; Figueiredo et al, J Clin Microbiol 2001:39:1339).

Therefore, there is a need for a diagnostic test for CagA+ *H. pylori* with improved diagnostic properties, for example improved specificity and sensitivity.

Furthermore, there is a great variability in the DNA-sequences among different *H. pylori* isolates. Certain CagA-variants are more strongly associated to gastric cancer risk. Therefore, it would also be useful to be able to identify the CagA strain type.

There is also a need for CagA-peptides that bind specifically to antibodies, in particular antibodies that bind to the CagA protein.

SUMMARY OF INVENTION

Herein it is provided information about peptides from CagA that are useful for diagnostic applications related to *H. pylori*-associated disease, including identification of individuals at high risk of gastric cancer development. *H. pylori*-infected individuals will raise antibodies against *H. pylori* proteins, including CagA. Thus, the presence of CagA-specific antibodies indicates *H. pylori* infection.

From all CagA peptides present in infected individuals, we have 1) defined which subset that is immunogenic and elicits an antibody-response (see Table 1, where 34% of the length of the protein is immunogenic). It turned out that many peptides react also with serum from non-infected patients (white bars in FIG. 1). Within the subset of immunogenic peptides, we have identified 2) the smaller subset of peptides that has a diagnostic capacity; and finally, in this subset of diagnostic peptides, we have 3) identified the crucial amino acid sequence(s) common to the peptides having the highest diagnostics capacity. In other words, the diagnostic capacity does not stem from only the presence/absence of peptides in the infected individual, but crucially also from only a small subset of the immunogenic peptides consistently eliciting an antibody-response that is absent in non-infected individuals.

By utilizing high-precision serology, with resolution at the peptide level instead of at protein level, we identified peptides to which there is a strong antibody-response only in individuals carrying CagA+ *H. pylori*, while excluding peptides that cause false positives due to a cross-reactive antibody-response in individuals lacking a CagA+ *H. pylori* infection. Therefore, the diagnostic peptides we have identified have both high sensitivity and specificity as determined by ROC AUC values, and will be useful for diagnostic applications.

In a first aspect of the invention there is provided a peptide comprising or consisting of an amino acid sequence selected from the group consisting of SEQ ID NO 1 to SEQ ID NO 7. Preferably said peptide consists of at most 25 amino acids, more preferably 15 amino acids and even more preferred at most 10 amino acids. In a preferred embodiment the peptide comprises or consists of the sequence selected from the group consisting of SEQ ID NO 2-7, or even more preferred the group consisting of SEQ ID NO 2-5.

These novel peptides have the advantage that they can be used for diagnosis, more specifically diagnosis of CagA-positive *H. pylori*. Thus, diagnosis using these peptides results in few false positives.

The minimal binding regions that have been identified are also useful for detecting CagA-specific antibodies. Since they are short, there will be low background binding. Furthermore, the peptides are short and can therefore be manufactured at a low cost.

In a second aspect of the invention there is provided a peptide according to the first aspect of the invention for use in diagnosis. In a preferred embodiment the diagnosis is diagnosis of *H. pylori* infection, more specifically CagA-positive *H. pylori*, or for prediction of the risk for gastric cancer.

In a third aspect of the invention there is provided a kit comprising a peptide according to the first aspect of the invention or a mixture of peptides according to the second aspect of the invention. The kit is preferably a kit for diagnosis, more specifically diagnosis of CagA-positive *H. pylori*, or for prediction of the risk for gastric cancer.

In a fourth aspect of the invention there is provided a method of diagnosis comprising the steps of a) isolating or providing a sample from a subject, b) contacting said sample with a peptide as described herein or a mixture of peptides as described herein, and c) detecting specific binding of antibodies in the sample to the peptide. The method is, in a preferred embodiment, used for detection of *H. pylori* infection or for the prediction of risk for gastric cancer.

In a fifth aspect of the invention there is provided a method for preventing gastric cancer in a subject comprising the steps of 1) carrying out diagnosis as described herein and 2) treating the *H. pylori* CagA+ infection in the subject. The method may comprise the steps of using the diagnosis method herein to determine that the subject has a *Helicobacter pylori* infection, and then treating the infection. The treatment may involve administering an antibiotic selected from a class of antibiotics the class of antibiotics selected from the group consisting of macrolides, beta-lactams, nitroimidazoles, tetracyclines and fluoroquinolones. The treatment may involve administering two antibiotics from said classes, where the two antibiotics are from different classes. The treatment may also involve administering a proton pump inhibitor to the subject, preferably in combination with antibiotics.

In a sixth aspect of the invention there is provided a method of detecting *H. pylori* CagA-binding antibodies in a sample from a subject, the method comprising contacting a biological sample with a peptide according to the first aspect of the invention and detecting binding of antibodies in the sample to the peptide. The sample may be a blood, serum, plasma sample or tissue sample, for example a gastric tissue sample.

In a seventh aspect of the invention there is provided a mixture of at least two peptides according to the first aspect of the invention. Such a mixture has the advantage that it can be used for detecting two or more different CagA-positive strains of *H. pylori* in an efficient manner. The mixtures can be in used the same manner as the peptides herein.

BRIEF DESCRIPTION OF DRAWINGS

FIG. 2 ROC AUC levels of all peptides tested from the 18 identified CagA epitopes (n=1144 peptides).

Figure 1:
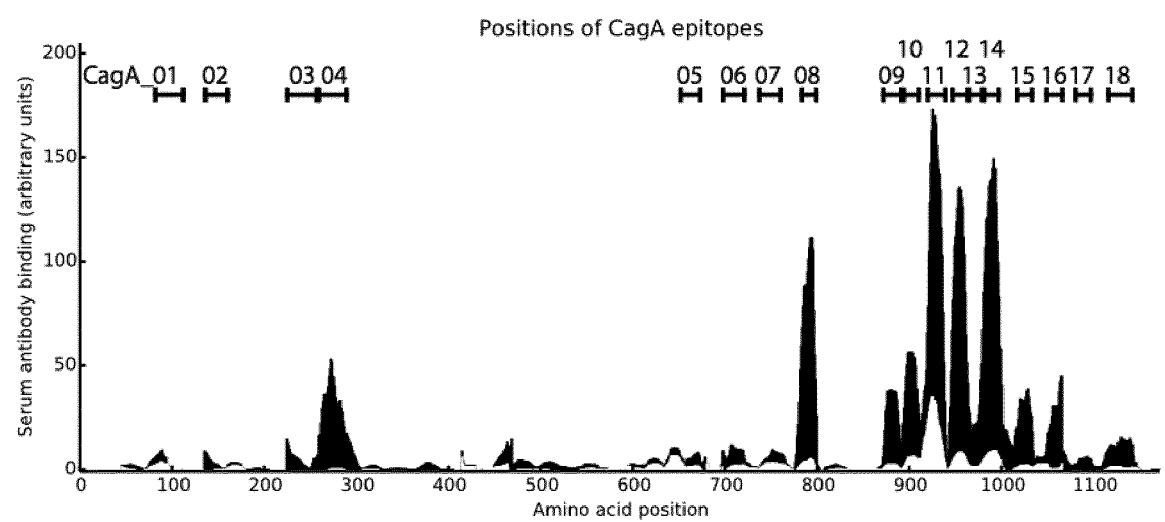
FIG. 1. Identification of 18 different linear B-cell epitopes of CagA using peptide microarray analysis. The array score for each peptide (n=1172 peptides) is shown as a vertical bar at the start position in the CagA sequence (x-axis). Black bars are results of sera from *H. pylori*-infected individuals, and white bars are results of sera from *H. pylori* uninfected individuals. Importantly, many peptides shown reactivity also with serum from non-infected individuals (white bars).

BT_300: IINQKVTDKVDNLNQ (SEQ ID NO 13) (at least 12 out of 15 amino acids identical, n=298 peptides);
BT_301: EPIYA (SEQ ID NO 8) (n=270);
BT_302: EPIYAK (SEQ ID NO 9) (n=16);
BT_303: EPIYAQ (SEQ ID NO 10) (n=21);
BT_304: EPIYT (SEQ ID NO 11) (n=21);
BT_305: EPIYAT (SEQ ID NO 12) (n=196);
BT_306: FXLKRHX (SEQ ID NO 1) (n=246);
BT_307: FXLKKHX (SEQ ID NO 2) (n=34);
BT_308: FXLKQHX (SEQ ID NO 3) (n=1);
BT_309: YXLKRHX (SEQ ID NO 4) (n=3);
BT_310: IXLKRHX (SEQ ID NO 5) (n=1);
BT_311: FXLRRYX (SEQ ID NO 6) (n=1);
BT_312: FXLRRSX (SEQ ID NO 7) (n=7).
AUC=0.5 is indicated as a dashed horizontal line.

DETAILED DESCRIPTION

Sometimes it is referred to an interval of sequences herein. This refers to all the sequences in the interval, thus for example "SEQ ID NO 2 to SEQ ID 5" refers to SEQ ID NO, 2, 3, 4, and 5. Sequences are written using the standard one-letter annotation for amino acid residues. The amino acid residues are preferably connected with peptide bonds.

Some peptides herein may have sequence variability. Thus, certain sequences may specify a position in the sequence that can be any amino acid. This may be indicated with an X or, in the sequence listing, Xaa. The X or Xaa can be replaced with any amino acid, preferably any L-amino acid, including amino acids resulting from post translational modification, such as citrulline. The amino acid does not have to be a naturally occurring amino acid. Preferably the amino acid does not have a bulky side chain, as a bulky side chain could prevent antibody binding. A suitable molecular weight of the amino acid may be from 85 D to 300 D, more preferably from 89 D to 220 D.

In general, the peptide may comprise or consist of an amino acid sequence selected from the group consisting of SEQ ID NO 1 to SEQ ID NO 330 The peptide may comprise of parts of the sequences of SEQ ID NO 32 to SEQ ID NO 330, for example 12, more preferred 13, even more preferred 14 and most preferred all 15 of the residues of SEQ ID NO 32 to SEQ ID NO 330. When the peptide comprises or consists of 12, 13, or 14 of the amino acids of SEQ ID NO 32-330, the other amino acid position may be replaced with any amino acid as described above for X and Xaa, while the remaining amino acids have the positions as in SEQ ID NO 32-330. In certain embodiments the amino acid may be replaced in a conserved manner, wherein, for example, a hydrophobic amino acid is replaced with a different hydrophobic amino acid, or where a polar amino acid is replaced with a different polar amino acid.

In some embodiments a peptide comprising or consisting of an amino acid sequence of SEQ ID NO 32 to SEQ ID NO 330 (table 2 and 3) may be preferred. In one embodiment a peptide comprising or consisting of one of SEQ ID NO 14 to SEQ ID NO 31 is used. In one embodiment a peptide comprising or consisting of one of SEQ ID NO 32 to SEQ ID NO 207 is used (Table 2). In one embodiment a peptide comprising or consisting of one of SEQ ID NO 208-330 is used (Table 3).

In a preferred embodiment a peptide comprising or consisting of one of SEQ ID NO 1 to SEQ ID NO 13 is used, for example SEQ ID NO 1, 2, 3, 4, 5, 6, 7, 8, 9, 10, 11, 12 or 13 (Table 4). These sequences comprise the minimal binding regions of certain antibodies. In a preferred embodiment the peptide comprises or consists of an amino acid sequence selected from SEQ ID NO 1 to SEQ ID NO 12.

In an even more preferred embodiment the peptide comprises or consists of a sequence selected from SEQ ID No 1 to SEQ ID NO 7. These peptides have the advantage that the diagnostic accuracy is higher, since they elicit a strong antibody-response in a high percentage of individuals carrying a CagA+ *H. pylori* infection. These peptides (SEQ ID NO 1 to SEQ ID NO 7) all relate to the same epitopes (epitope 12 and 14), and around 95% of all CagA+ *H. pylori* isolates of the world carry at least one of these sequence variants. Furthermore, the peptides have common structural features in that:

They all have seven amino acid residues.

They all have a hydrophobic residue in the first position (F, Y or I).
They all have x in the second position.
They all have an L in the third positon.
They all have K or R (positive side chains) in the fourth position,
They all have an x in the seventh position.

Examples of useful peptides that comprise SEQ ID NO 1 to SEQ ID NO 7 include, but is not limited to, sequences SEQ ID NO 129 to SEQ ID NO 170, SEQ ID NO 186 to SEQ ID NO 187 and SEQ ID NO 266 to SEQ ID NO 279.

In an even more preferred embodiment the peptide comprises or consists of a sequence selected from SEQ ID NO 1, 2, 3, 4 and 5, or even more preferred, one or more sequences selected from the group consisting of SEQ ID NO 2, 3, 4, 5, 6, and 7 or even more preferred SEQ ID NO 2, 3, 4 and 5. Examples of useful peptides that comprise these sequences are described in Table 2 and 3.

In one embodiment the peptide comprises or consist of the sequence of SEQ ID NO 13, or a sequence of twelve amino acid residues selected from that sequence, where the other three amino acid residues can be any amino acid, as described above. Useful amino acid sequences that comprise at least twelve amino acids from SEQ ID NO 13 include, but is not limited to, sequences SEQ ID No 52 to SEQ ID NO 67 and SEQ ID NO 235 to SEQ ID NO 256.

In one embodiment the peptide comprises or consists of the sequence of SEQ ID NO 153, or a sequence of 12, 13 or 14 amino acids selected from that sequence, where the other amino acid residues can be any amino acid, as described above.

The peptide preferably has a length of 25 amino acids or shorter, such as 20 or 15 amino acids. A shorter peptide may be desirable because it results in less unspecific binding (by an antibody) and therefore less background. However, a longer peptide may in some cases be desirable to allow for exposing the epitope to allow antibody binding without sterical hindrance, or for peptide folding. Thus, more preferably the peptide is 14 amino acid residues, more preferably 13 amino acid residues, even more preferably 12, 11, 10, 9, 8, 7, 6 or 5 amino acid residues (6 applies to SEQ ID 8, 11, 9, 10 and 12 only, and 5 applies to SEQ ID NO 8 and 11 only).

Preferably the peptide binds specifically (in the immunological sense) and with high affinity to an antibody, preferably an antibody that also binds to the *H. pylori* CagA protein. An antibody-peptide interaction is said to exhibit "specific binding" or "preferential binding" in the immunological sense if it reacts or associates more frequently, more rapidly, with greater duration and/or with greater affinity with a particular cell or substance than it does with alternative cells or substances. An antibody "specifically binds" or "preferentially binds" to a peptide if it binds with greater affinity, avidity, more readily, and/or with greater duration than it binds to other substances. Binding can be determined with any suitable method. Binding can be determined by methods known in the art, for example ELISA, surface plasmon resonance, western blot or the other methods described herein (see below). Such methods can be used for determining suitable length or amino acid sequence of the peptide.

Preferably the use of the peptide has both a high diagnostic specificity and a high diagnostic sensitivity. In any diagnostic test, these two properties are dependent on what level is used as the cut-off for a positive test. To assess diagnostic accuracy independently of a set cut-off, a receiver operator characteristic curve (ROC curve) can be used. In an ROC curve, true positive rate (sensitivity) is plotted against false positive rate (1-specificity) as the cut-off is varied from 0 to infinity. The area under the ROC curve (ROC AUC) is then used to estimate the overall diagnostic accuracy. Preferably the use of the peptide has an ROC AUC of at least 0.55, for example an ROC AUC of at least, 0.60, 0.65, 0.70, 0.75, 0.80, 0.85, 0.90, 0.95, 0.96, 0.97, 0.98, 0.99 or an ROC AUC of 1.00. Preferably, the use of the peptide has ROC AUC of at least 0.85, and most preferably an ROC AUC of 1.

As used herein, the term "peptide" is used to mean peptides, proteins, fragments of proteins and the like, including peptidomimetic compounds. The term "peptidomimetic", means a peptide-like molecule that has the activity of the peptide upon which it is structurally based, the activity being specific and high affinity binding to antibodies that bind to the CagA protein. Such peptidomimetics include chemically modified peptides, peptide-like molecules containing non-naturally occurring amino acids (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). A variety of peptidomimetics are known in the art including, for example, peptide-like molecules which contain a constrained amino acid. In certain embodiments circular peptides may be used.

The peptide may be an isolated peptide meaning a peptide in a form other than it occurs in nature, e.g. in a buffer, in a dry form awaiting reconstitution, as part of a kit, etc.

In some embodiments, the peptide is substantially purified meaning a peptide that is substantially free of other proteins, lipids, carbohydrates, nucleic acids and other biological materials with which it is naturally associated. For example, a substantially pure peptide can be at least about 60% of dry weight, preferably at least about 70%, 80%, 90%, 95%, or 99% of dry weight.

A peptide of the present invention can be in the form of a salt. Suitable acids and bases that are capable of forming salts with the peptides are well known to those of skill in the art, and include inorganic and organic acids and bases.

The peptide can be provided in a solution, for example an aqueous solution. Such a solution may comprise suitable buffers, salts, protease inhibitors, or other suitable components as is known in the art.

The peptide may be associated with (e.g. coupled, fused or linked to, directly or indirectly) one or more additional moieties as is known in the art. Non-limiting examples of such moieties include peptide or non-peptide molecules such as biotin, a poly his tag, GST, a FLAG-tag, or a linker or a spacer. The association may be a covalent or non-covalent bond. The association may be, for example, via a terminal cysteine residue or a chemically reactive linking agent, the biotin-avidin system or a poly-his tag. For example, the peptide may be linked with a peptide bond to a single biotin-conjugated lysine residue, in which the lysine is biotinylated via the epsilon amino groups on its side chain, such as the peptide example H-XXXXXXXXXXXXXXX (K(Biotin))-NH2, (SEQ ID NO 331) where X indicates the amino acids of the peptide.

The associated moiety may be used to attach or link the peptide, to improve purification, to enhance expression of the peptide in a host cell, to aid in detection, to stabilize the peptide, etc. In the case of a short peptide attached to a substrate, for example a solid phase, it may be desirable to use a linker or a spacer to ensure exposure of the peptide to antibodies so that the antibodies can bind.

The peptide may be associated with a substrate that immobilizes the peptide. The substrate may be, for example, a solid or semi-solid carrier, a solid phase, support or surface. The peptide may be immobilized on a solid support. Examples includes beads or wells in plates, such as microtiter plates, such as 96-well plates, and also include surfaces of lab-on-a-chip diagnostic or similar devices. The association can be covalent or non-covalent, and can be facilitated by a moiety associated with the peptide that enables covalent or non-covalent binding, such as a moiety that has a high affinity to a component attached to the carrier, solid phase, support or surface. For example, the biotin-avidin system can be used.

The peptides can be used for detecting H. pylori CagA-specific antibodies in a sample from a subject, the method comprising contacting a biological sample with a peptide as described herein and detecting binding of antibodies in the sample to the peptide. The peptide may be associated with a substrate that immobilizes the peptide, as described herein, for example attached to a solid support. The method may include incubation to allow binding, washing, and detection of antibodies as described herein. Methods for detecting binding of antibodies are described below and include for example ELISA.

The peptides can be used for diagnosis, in particular diagnosis of infection of H. pylori or gastric cancer. It is known that CagA H. pylori infection correlates with an increased risk for gastric cancer. Thus, the peptides can be used for assessing the risk of a subject developing gastric cancer. The risk of developing gastric cancer may include the risk of proceeding from not having gastric cancer to having gastric cancer of any stage, of proceeding from a benign disease state to a malign state or proceeding from a less malign state to a more malign state. Thus, the risk may include the risk of having gastric cancer or developing gastric cancer in the future. In a preferred embodiment the peptide is used for assessing the risk of a subject developing gastric cancer in the future. The peptides can also be used for diagnosis of other diseases that are associated with H. pylori infection, such as peptic ulcer disease, dyspepsia and immune thrombocytopenic purpura (ITP).

Diagnosis can be carried out using any suitable method. In a preferred method, antibodies in a sample from a subject are allowed to bind to a peptide, and binding is detected. The subject can be a human or an animal, preferably a human. Binding in vitro of antibodies from the subject to the peptide indicates that the immune system of the subject has generated antibodies against that particular peptide and thus that that peptide and hence that CagA H. pylori is present in the subject.

The method may comprise the steps of (1) isolating, from a subject, a sample of body fluid or tissue likely to contain antibodies or providing, in vitro, such a sample; (2) contacting the sample with a peptide, under conditions effective for the formation of a specific peptide-antibody complex (for specific binding of the peptide to the antibody), e.g., reacting or incubating the sample and a peptide; and (3) assaying the contacted (reacted) sample for the presence of an antibody-peptide reaction (for example determining the amount of an antibody-peptide complex). The method may involve one or more washing steps, as is known in the art. Steps 2 and 3 are preferably carried out in vitro, that is. using the sample after the sample has been isolated from the subject, in a sample previously isolated from a subject.

The sample can be any suitable sample for example a sample of blood, serum, plasma, saliva, mucosal secretion, ascites fluid, or similar bodily fluid, or tissue.

Antibody-response to the peptides can be detected by different immunological/serological methods. Suitable formats of detecting presence of the antibody using the peptides includes peptide micro arrays, ELISA, chromatography, western blot, lab-on-a chip formats, microbead-based single- or multiplex immunoassays etc.

Often these methods involve proving the peptide bound to stationary phase (such as the well of an ELISA plate or the surface of a microbead) and adding the sample to be analysed in the liquid phase, allowing antibodies to bind and then washing away unbound antibodies.

Antibody binding can be detected in vitro by using a labelled secondary antibody that binds to a specific type of human antibody for example IgG, IgA, IgG1, IgG2 or IgG3, IgG4. In ELISA, the secondary antibody is labelled with an enzyme, such as horseradish peroxidase (HRP) or alkaline phosphatase (AP). The secondary antibody is suitably from another species than human, for example from rabbit or goat.

Alternatively, a fluorescence label or radioactive label can be used.

A protocol for using the peptides in an ELISA can be easily optimized by a person skilled in the art with regard to which secondary antibody to use, its dilution, buffers, blocking solution, wash etc. An outline of an example of an ELISA protocol using plates can be as follows: Polystyrene microtiter plates are coated with optimal concentrations, as determined by checkerboard titrations, of the peptides of interest dissolved in PBS at room temperature overnight. After two washes with PBS, wells are blocked with 0.1% (wt/vol) bovine serum albumin-PBS at 37° C. for 30 min. Subsequent incubations are performed at room temperature, and plates are washed three times with PBS containing 0.05% Tween (PBS-Tween) between incubations. Samples of serum or other bodily fluids are added in duplicates or triplicates in initial dilutions of for example $^1/_{10}$, and diluted for example in a three-fold dilution series. Control samples previously tested and found to have antibodies to the peptides are used as positive controls. Samples with known concentration of antibodies may be used for creating a standard curve. Wells to which only PBS-Tween are added are used as negative controls for determination of background values. After incubation at room temperature for 90 min, HRP-labeled rabbit anti-human IgA or IgG antibodies are added and incubated for 60 min. Plates are thereafter read in a spectrophotometer 20 min after addition of $H_2O_2$ and ortho-phenylene-diamine dihydrochloride in 0.1 M sodium citrate buffer, pH 4.5. The end point titers of each sample are determined as the reciprocal interpolated dilution giving an absorbance of for example 0.4 above background at 450 nm. Alternatively, as the final read-out value, the absorbance value can be used. The skilled person recognized that this ELISA protocol is an example only and many different variants and alterations of this protocol are possible.

Alternatively, in one embodiment, B-cells are isolated from the subject, and it is analysed if the cells are able to produce antibodies that bind to the peptide. This can be done by using the ELISPOT method, ALS (antibodies in lymphocyte secretions), or similar methods.

Diagnosis can also be carried out by detecting the presence of CagA protein in tissue sample from a patient using antibodies specific for a peptide selected from peptides comprising or consisting of SEQ ID NO 32-330, SEQ ID NO 1-7, in particular SEQ ID NO 2-5. The sample is preferably a sample of gastric tissue. Antibodies with the desired binding specificity can be generated by a person skilled in the art. The antibody can be a polyclonal or a monoclonal antibody, where monoclonal antibodies are preferred. The antibody can be used in any useful format to detect the protein, for example western blot, ELISA, immunohistochemistry, etc. The antibody can be used for the diagnostic methods herein.

The method may be such that it can result in two possible outcomes: H. pylori infection present or H. pylori infection absent. H. pylori infection can for example be determined on the basis of a signal cut off in the assay. There may also be an intermediate result: outcome uncertain that warrants further investigation or re-sampling or reanalysis of samples.

Once it has been established that a CagA+ H. pylori infection is present it may be useful to treat the H. pylori infection, for example in order to decrease the risk of the subject developing gastric cancer. Treatment can be done by methods known in the art, for example with the use of antibiotics. For different reasons, some being low availability of active antibiotics in the stomach as well as problems with antibiotic resistance, there are many different antibiotic treatment regimens for H. pylori infection, and the efficacy of these generally differ in different parts of the world. In general, the treatment regimens include at least two different antibiotics selected from the groups of macrolides, beta-lactams, nitroimidazoles, tetracyclines and fluoroquinolones, with or without the addition of bismuth subcitrate potassium, where one antibiotic is preferably selected from each group. One or more antibiotics may be administered in combination with a proton pump inhibitor. One treatment includes administration of the proton pump inhibitor omeprazole, and the antibiotics amoxicillin and clarithromycin for 7 to 14 days.

Thus, there is also provided a method for preventing gastric cancer comprising the steps of 1) carrying out diagnosis as described herein on a subject and 2) treating the H. pylori infection in the subject. Preferably treatment is made so that the subject is free of H. pylori infection.

Once it has been established that a CagA+ H. pylori infection is present it may also be useful to perform further investigations to assess the presence of gastric cancer of an early or advanced stage. This may be relevant for all patients, but is of special relevance in subjects known or suspected to otherwise have a high risk of gastric cancer, such as patients originating from countries with high gastric cancer risk, subjects who are smokers, and/or subjects whose close family members are known to have been diagnosed with gastric cancer. Such investigation can be made with gastroscopy, where the stomach lining is inspected to evaluate if gastric cancer is present. If a gastric tumour is observed, the tumour may be treated by endoscopic resection, if at an early stage, or by surgery, if at an advanced stage.

Alternatively, the method can be used as a follow-up to a routine gastroscopy investigation. If the endoscopy and/or the subsequent histopathology examination discover that there are precancerous conditions present in the stomach, for example by an elevated OLGA-score, the method can be used to inform further patient handling. This can be in the form of a recommendation for appropriate time-interval for follow-up gastroscopy. For example, if it has been established that a CagA+ H. pylori infection is present, it may be beneficial to perform a follow-up gastroscopy with a shorter time-interval than if there is no CagA+ H. pylori infection present.

The peptides can be synthesized by methods known in the art. The peptides can be obtained pure and in large quantities by means of organic synthesis, such as solid phase synthesis. Methods for peptide synthesis are well known in the art, for example using a peptide synthesis machine. Of course, the peptides may be ordered from a peptide synthesis company.

The peptides can also be of animal, plant, bacterial or virus origin. The peptide may then be purified from the organism, as is known in the art. The peptide can be produced using recombinant technology, for example using eukaryotic cells, bacterial cells, or virus expression systems. It is referred to Current Protocols in Molecular Biology, (Ausubel et al, Eds.) John Wiley & Sons, NY (current edition) for details.

H. pylori displays some genetic diversity in the CagA sequence and it may be desirable to use a peptide or a group of peptides that identifies several strains. SEQ ID NO 1 to SEQ ID NO 7 represents such a group of peptides, since 95% of all CagA+ H. pylori isolates of the world carry at least one of these sequence variants. Thus, it may be useful to provide a mixture (a "cocktail") of two or more peptides herein (SEQ ID NO 1-330). In one embodiment such a mixture comprises at least two, preferably three, more preferably four, more preferably five, more preferably six and more preferably seven peptides selected from peptides that comprise or consist of SEQ ID NO 1 to SEQ ID NO 13. In one embodiment the sequences are selected from SEQ ID NO 1 to SEQ ID NO 7. Preferred mixtures include SEQ ID NO 1, 2, 3, 4, 5, 6 and 7, SEQ ID NO SEQ ID NO 1, 2, 3, 4 and 5, SEQ ID NO 2, 3, 4, 5, 6, and 7 and SEQ ID NO 2, 3, 4 and 5. SEQ ID NO 1 to SEQ ID NO 5 are present in the so called CagA ABC, ABCC and ABCCC types, while SEQ ID NO 6 and SEQ ID NO 7 are only present in the ABD type. Thus, in one embodiment one sequence is selected from SEQ ID NO 1 to 5 and one sequence is selected from one of SEQ ID NO 6 and 7. The peptides of SEQ ID NO 6 and 7 may be particularly useful for diagnosis of H. pylori strains in Asia.

Another useful way to detect more than one H. pylori strain is to use a peptide containing the motif EPIYA (SEQ ID NO 332), which is present in SEQ ID NO 8, 9, 10 and 12.

One or more peptides may be included in a kit. The kit may be used for diagnosis as described herein. A kit may comprise one or more peptides or mixtures thereof, binding buffer, and detection agents such as a secondary antibody. The kit can include a substrate that immobilizes the peptide, such as a solid support, such as microtiter plates, such as ELISA plates to which the peptide(s) of the invention have been pre-adsorbed, various diluents and buffers, labelled conjugates or other agents for the detection of specifically bound antigens or antibodies, such as secondary antibodies, and other signal-generating reagents, such as enzyme substrates, cofactors and chromogens. Other suitable components of a kit can easily be determined by one of skill in the art.

EXAMPLES

Example 1

CagA-peptides of relevance were identified using a three-step procedure, using peptide array experiments. The antibody binding signature of the peptides was analyzed by incubating the arrays with pooled or individual serum samples from H. pylori-infected and uninfected individuals from a dyspepsia patient cohort. The H. pylori-infected individuals had an infection with known CagA-status (cagA-gene present/absent).

Serum samples were obtained from individuals in Managua, Nicaragua undergoing endoscopy due to dyspepsia, as previously described (Thorell et al, BMC Evol Biol 2016: 16:53). Each of these patients had a known *H. pylori* infection status, and the genome sequences of their *H. pylori* isolates were available.

Published genomic sequences of *H. pylori* were obtained from NCBI. Available complete genomes (n=49) for *H. pylori* were downloaded from GenBank in August 2013. The experimental strains B8, Rif1, Rif2, UM298, and UM299 were removed and the remaining 44 complete strains were used for comparative genomics. The whole-genome sequenced isolates available in GenBank as of 2013-11-01 were downloaded, and all isolates containing open reading frame information were used but for strains passaged in animals or experimentally derived strains. The previously published Nicaraguan genome sequences from the Sequence Read Archive database under accession number SRP045449 were also used.

In addition to these publically available genome sequences, sequences of *H. pylori* strains isolated in Australia were obtained from professor Barry J Marshall (University of Western Australia, WA, Australia).

To identify the deduced CagA protein sequences within the available genomes, a similarity search using blastp was performed using the CagA sequence from strain 26695 (NC_000915.1). In our collection of genome sequences, 245 strains/isolates were found to contain the cagA gene, and all deduced CagA protein sequences of these isolates were used for subsequent analysis.

Example 2

Antibody-responses to CagA-peptides were assayed using peptide array analysis. Medium-density arrays were printed using laser printing synthesis technology. On these chips, around 8 600 different 15-amino acid (15-mer) *H. pylori* peptides were spotted onto each chip. Thereafter, the chips were incubated with a 1/1000-dilution of patient serum, or a 1/1000-dilution of a pool of 10 different serum samples, followed by washing and subsequent incubation by fluorochrome-conjugated rabbit anti-human-IgG antibodies. Finally, fluorescence image scanning and digital image analysis was performed to detect antibody-binding to each of the peptides on the chip. Chip printing and antibody analysis was performed by the company PEPperPRINT (Heidelberg, Germany).

Example 3

High-density arrays were made using on-chip photolithographic synthesis. In these experiments, around 200 000 different 15-mer *H. pylori* peptides were spotted onto each chip. Thereafter, the chips were incubated with 1/1000-dilution of patient serum, or a 1/1000-dilution of a pool of 10 different serum samples, followed by washing and subsequent incubation by fluorochrome-conjugated rabbit anti-human-IgG or rabbit-anti-human-IgA antibodies. Finally, fluorescence image scanning and digital image analysis was performed to detect antibody-binding to each of the peptides on the chip. Chip printing and antibody analysis was performed by the company Schafer-n (Copenhagen, Denmark).

Example 4—Identification of B-cell Epitopes of CagA

The entire CagA-sequence was screened by assessing serum antibody-binding to overlapping 15-mer peptides and pools of serum samples. Medium-density arrays of example 2 spotted with peptides covering the entirety of the CagA-sequence, with a sequential overlap of 10 amino acids (n=234 peptides) were used. In follow-up experiments, high-density arrays of example 3 with 15-mer peptides covering the entirety of the CagA-sequence were used, but this time with a sequential overlap of 14 amino acids (n=1172 peptides). In both cases, the *H. pylori* strain 26695 was used as the source of the CagA peptide sequences. Antibody-binding to each peptide was assessed individually on the array, and two serum pools—one consisting of pooled sera from 10 *H. pylori*-infected (Hp+) individuals and the other consisting of sera from 10 uninfected (Hp−) individuals were used.

The antibody-binding of the Hp+ serum pool was compared to the binding of the Hp− pool. A linear B-cell epitope was defined as a stretch of at least four amino acids where the antibody-binding was at least 2× higher in the Hp+ group than in the Hp− group. In this way it was determined that *H. pylori* CagA contains 18 different linear B-cell epitopes, with an average length of 22 amino acids (Table 1 and FIG. 1). These epitopes are all useful for diagnosis of a CagA+ *H. pylori*-infection.

TABLE 1

| SEQ ID | Epitope | Amino acid sequence | Start[1] | End[1] | Length |
|---|---|---|---|---|---|
| 14 | CagA_01 | NPTKKNQYFSDFIDKSNDLINKDNLIDVESS | 80 | 110 | 31 |
| 15 | CagA_02 | DPSKINTRSIRNFMENIIQPPIPDD | 134 | 158 | 25 |
| 16 | CagA_03 | KKQSSDVKEAINQEPVPHVQPDIATTTTDIQGL | 223 | 255 | 33 |
| 17 | CagA_04 | PEARDLLDERGNFSKFTLGDMEMLDVEGVAD | 257 | 287 | 31 |
| 18 | CagA_05 | KAQANSQKDEIFALINKEANRD | 650 | 671 | 22 |
| 19 | CagA_06 | SKDLKDFSKSFDEFKNGKNKDFSK | 696 | 719 | 24 |
| 20 | CagA_07 | GINPEWISKVENLNAALNEFKNGK | 735 | 758 | 24 |
| 21 | CagA_08 | INQKVTDKVDNLNQAVS | 781 | 797 | 17 |
| 22 | CagA_09 | FSDIKKELNEKFKNFNNNNN | 870 | 889 | 20 |
| 23 | CagA_10 | KNSTEPIYAKVNKKKTG | 892 | 908 | 17 |
| 24 | CagA_11 | YTQVAKKVNAKIDRLNQIAS | 918 | 937 | 20 |
| 25 | CagA_12 | AAGFPLKRHDKVDDLSK | 945 | 961 | 17 |
| 26 | CagA_13 | GLSASPEPIYATIDD | 963 | 977 | 15 |
| 27 | CagA_14 | GGPFPLKRHDKVDDLSK | 979 | 995 | 17 |
| 28 | CagA_15 | VSEAKAGFFGNLEQTID | 1015 | 1031 | 17 |
| 29 | CagA_16 | ESAKKVPASLSAKLDNYA | 1047 | 1064 | 18 |

TABLE 1-continued

| SEQ ID | Epitope | Amino acid sequence | Start[1] | End[1] | Length |
|---|---|---|---|---|---|
| 30 | CagA_17 | GAINEKATGMLTQKNPEW | 1078 | 1095 | 18 |
| 31 | CagA_18 | SEYDKIGFNQKNMKDYSDSFKFSTKLN | 1114 | 1140 | 27 |

[1]Start and end positions refer to the amino acid positions in CagA of the strain 26695.

Example 5—Identification of 15-mer CagA Peptides with High Diagnostic Potential Individual serum samples were assayed for antibody binding to the identified epitopes, to assess the frequency with which *H. pylori*-infected individuals having or lacking CagA+ *H. pylori* react with antibodies to the different epitopes. Since the 18 epitopes each spanned more than one 15-mer peptide, again overlapping peptides were used, this time with a 10- or 11-amino acid overlap between sequential peptides. Furthermore, since there is a considerable sequence diversity of CagA in different *H. pylori* isolates, sequence variants for each peptide were included. Thus, for each overlapping 15-mer peptide sequence from 26695 CagA, every available sequence variant of this peptide was also used, if such a sequence variant was found present at least twice in our database of 245 world-wide CagA sequences. In total, 1144 different CagA peptides and sequence variants within the 18 identified epitopes were assayed using high-density arrays. Each peptide was assayed with individual serum samples (n=48) from individuals with or without CagA+ *H. pylori*-infection, and from uninfected controls.

Epitopes with a high frequency of responding individuals and a strong antibody binding would be suitable to use for diagnosis of CagA+ *H. pylori* infection. A problem with previously known methods to assess CagA-antibodies has been the high number of false-positive individuals—i.e. *H. pylori*-non-infected individuals that comes out positive in the test. Therefore, those peptides that had a good discriminatory capacity were identified: a strong antibody-response in individuals with a CagA+ infection, but a minimal response in those with an infection lacking CagA, and in *H. pylori*-uninfected individuals.

The discriminatory capacity of peptides using ROC curves were assayed and the area under the curve (AUC) of the ROC curve (ROC AUC) was used as an estimation of diagnostic capacity.

Figure 2A:
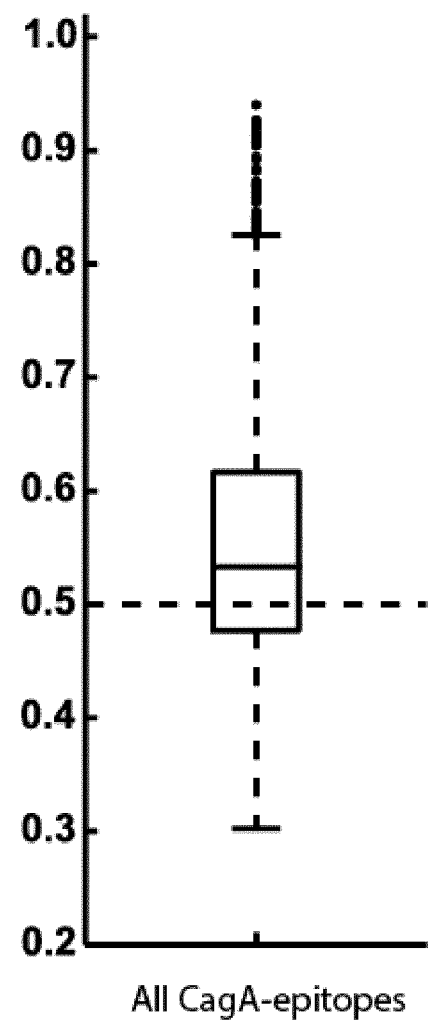
FIG. 2a: Results shown as box plot, including median, interquartile range and outliers.

The median ROC AUC of 1144 different peptides, including sequence variants, from the 18 identified CagA epitopes was 0.53 (FIG. 2A). Since an ROC AUC of 0.53 is very close to the diagnostic accuracy of a coin-toss (i.e. not useful for diagnosis), this highlights the problem of high false-positive rates for existing serology tests relying on antibody-responses to the entire CagA protein.

Figure 2B:
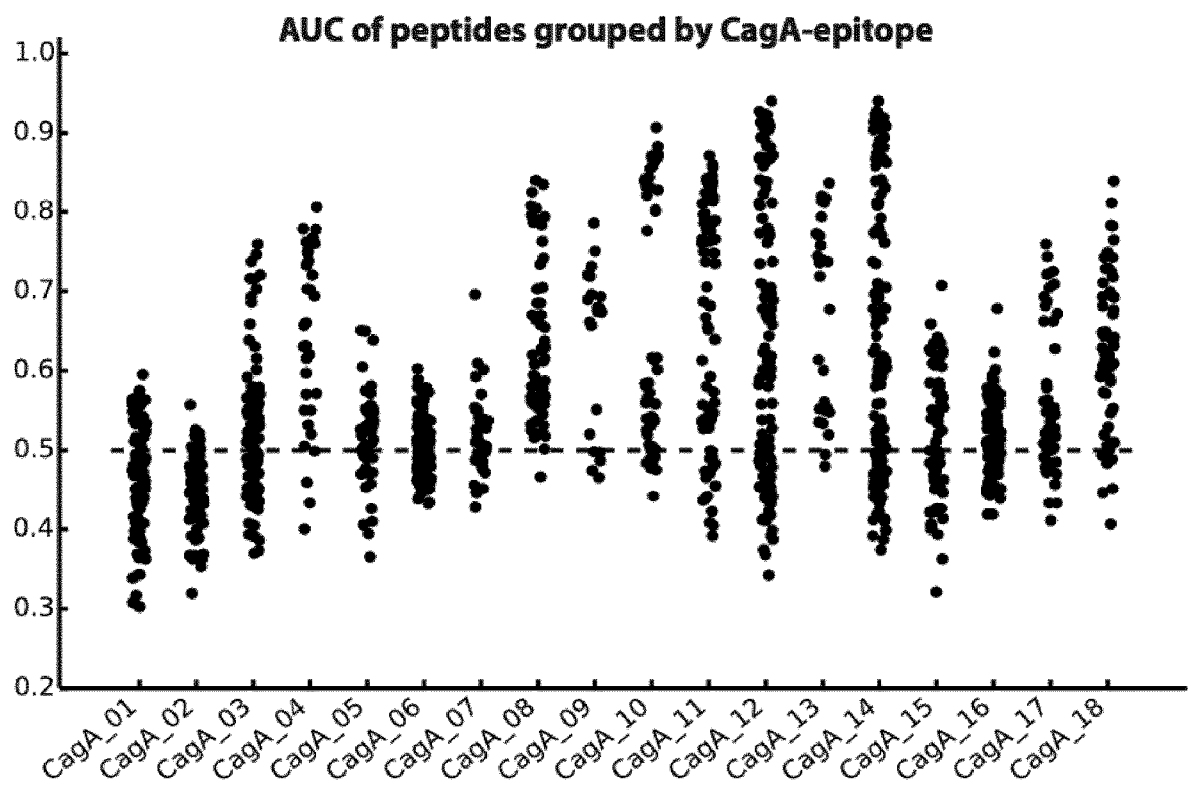
FIG. 2b: Results for each individual peptide are shown, grouped by epitope. In both 2a and 2b, the AUC of a useless diagnostic (AUC=0.5) is indicated as a dashed horizontal line.

There was an uneven distribution of ROC AUC among different epitopes, with epitopes 3-4, 8-14, and 17-18 containing most of the peptides with a high diagnostic capacity (FIG. 2B).

Among the 1144 peptides, 176 CagA peptides with an ROC AUC higher than 0.7 were identified (Table 2). Each of these peptides can be used for diagnosis of *H. pylori* CagA+ infection.

TABLE 2

| SEQ ID NO | Name | Sequence | AUC | Epitope |
|---|---|---|---|---|
| 32 | BT_001 | DVKEAINQEPVPHVQ | 0.72 | CagA_03 |
| 33 | BT_002 | DVKEAINQEPLPHVQ | 0.76 | |
| 34 | BT_003 | DVKEAINQEPVPHIQ | 0.74 | |
| 35 | BT_004 | DVKEAINQEPVPNVQ | 0.72 | |
| 36 | BT_005 | TTTHIQGLPPESRDL | 0.70 | |
| 37 | BT_006 | TTTPIQGLPPESRDL | 0.72 | |
| 38 | BT_007 | TPTHIQGLPPEARDL | 0.75 | |
| 39 | BT_008 | QGLPPESRDLLDERG | 0.73 | CagA_04 |
| 40 | BT_009 | QGLPPEARDLLDERG | 0.75 | |
| 41 | BT_010 | QSLPPEARDLLDERG | 0.78 | |
| 42 | BT_011 | QGLPLEARDLLDERG | 0.74 | |
| 43 | BT_012 | ESRDLLDERGNFSKF | 0.72 | |
| 44 | BT_013 | LDERGNFFKFTLGDM | 0.70 | |
| 45 | BT_014 | NFSKFTLGDMEMLDV | 0.76 | |
| 46 | BT_015 | NFFKFTLGDVEMLDV | 0.70 | |
| 47 | BT_016 | NFSKFTLGDMNMLDV | 0.81 | |
| 48 | BT_017 | DFSKFTLGDMEMLDV | 0.77 | |
| 49 | BT_018 | NFFKFTLGDMEMLDV | 0.75 | |
| 50 | BT_019 | NFPKFTLGDMEMLDV | 0.78 | |
| 51 | BT_020 | NFSKFTLGDVEMLDV | 0.76 | |
| 52 | BT_021 | IKDVIINQEITDKVD | 0.74 | CagA_08 |
| 53 | BT_022 | IINQKITDKVDNLNQ | 0.81 | |
| 54 | BT_023 | IINQKVTDKVDNLNQ | 0.83 | |
| 55 | BT_024 | IINQKITDKVDDLNQ | 0.79 | |
| 56 | BT_025 | IINQKITDKVDNLSQ | 0.78 | |
| 57 | BT_026 | IINQKITDKVDNLSS | 0.84 | |
| 58 | BT_027 | IINQKVTDKVDDLNQ | 0.79 | |
| 59 | BT_028 | IINQEITDKVDNLNQ | 0.76 | |
| 60 | BT_029 | IINQKITDKADNLNQ | 0.80 | |
| 61 | BT_030 | IINQKVTDKVDNLSS | 0.80 | |
| 62 | BT_031 | IINQKITDKVDSLNQ | 0.84 | |
| 63 | BT_032 | IINQKITDKVENLNQ | 0.73 | |
| 64 | BT_033 | HINQQITDKVDNLNQ | 0.79 | |
| 65 | BT_034 | IFNQKITDKVDDLNQ | 0.79 | |
| 66 | BT_035 | ITDKVDNLNQAVSIA | 0.70 | |
| 67 | BT_036 | ITDKVDNLNQAVSEA | 0.70 | |
| 68 | BT_037 | TLAKNFSDIKKELNE | 0.73 | CagA_09 |
| 69 | BT_038 | TLSKNFSDIKKELNE | 0.72 | |
| 70 | BT_039 | NLAKNFSDIKKELNE | 0.72 | |
| 71 | BT_040 | NFSDIKKELNEKFKN | 0.79 | |
| 72 | BT_041 | NFSDIKKELNEKLFG | 0.75 | |
| 73 | BT_042 | KNSTEPIYAKVNKKK | 0.84 | CagA_10 |
| 74 | BT_043 | GLKNEPIYAKVNKKK | 0.87 | |
| 75 | BT_044 | KNNTEPIYAQVNKKK | 0.80 | |
| 76 | BT_045 | KNSGEPIYAQVNKKK | 0.78 | |
| 77 | BT_046 | KGPEEPIYAKVNKKK | 0.83 | |
| 78 | BT_047 | KNSAEPIYAQVNKKK | 0.80 | |
| 79 | BT_048 | KNSGEPIYAKVNKKK | 0.84 | |
| 80 | BT_049 | KNSAEPIYAKVNKKK | 0.86 | |
| 81 | BT_050 | ENSTEPIYAKVNKKK | 0.91 | |
| 82 | BT_051 | KNNEEPIYAQVNKKK | 0.88 | |
| 83 | BT_052 | KNNTEPIYAKVNKKK | 0.86 | |
| 84 | BT_053 | EPIYAKVNKKKTGQV | 0.87 | |
| 85 | BT_054 | EPIYAQVNKKKTGQV | 0.85 | |
| 86 | BT_055 | EPIYAKVNKKKAGQA | 0.87 | |
| 87 | BT_056 | EPIYAKVNKKKTGQA | 0.87 | |
| 88 | BT_057 | EPIYAKVNKKKAGQV | 0.87 | |
| 89 | BT_058 | EPIYAQVNKKKTGQA | 0.83 | |
| 90 | BT_059 | EPIYAQVNKKKAGQA | 0.82 | |
| 91 | BT_060 | EPIYAQVNKKKAGQV | 0.83 | |
| 92 | BT_061 | EPIYAKVNKKKTGEV | 0.84 | |
| 93 | BT_062 | EPIYAKVNKKKTEQA | 0.87 | |
| 94 | BT_063 | VASPEEPIYAQVAKK | 0.78 | CagA_11 |
| 95 | BT_064 | VASPEEPIYTQVAKK | 0.78 | |
| 96 | BT_065 | AASPEEPIYAQVAKK | 0.79 | |
| 97 | BT_066 | ATSPEEPIYAQVAKK | 0.80 | |
| 98 | BT_067 | AASLEEPIYAQVAKK | 0.78 | |
| 99 | BT_068 | AASPEEPIYTQVAKK | 0.76 | |
| 100 | BT_069 | AASHEEPIYAQVAKK | 0.79 | |
| 101 | BT_070 | VASLEEPIYTQVAKK | 0.75 | |
| 102 | BT_071 | LENSTEPIYTQVAKK | 0.74 | |

TABLE 2-continued

| SEQ ID NO | Name | Sequence | AUC | Epitope |
|---|---|---|---|---|
| 103 | BT_072 | ASPEEPVYTQVAKMV | 0.81 | |
| 104 | BT_073 | VASHEEPIYAQVAKK | 0.79 | |
| 105 | BT_074 | EEPIYAQVAKKVNAK | 0.86 | |
| 106 | BT_075 | EEPIYTQVAKKVNAK | 0.79 | |
| 107 | BT_076 | EEPIYAQVAKKVSAK | 0.87 | |
| 108 | BT_077 | EEPIYAQVAKKVTQK | 0.86 | |
| 109 | BT_078 | EEPIYAQVAKKVTKK | 0.82 | |
| 110 | BT_079 | EEPIYTQVAKKVTKK | 0.77 | |
| 111 | BT_080 | EEPIYTQVAKKVKAK | 0.76 | |
| 112 | BT_081 | EEPIYTQVAKKVTQK | 0.80 | |
| 113 | BT_082 | TEPIYTQVAKKVKAK | 0.75 | |
| 114 | BT_083 | EEPVYTQVAKMVTQK | 0.77 | |
| 115 | BT_084 | AQVAKKVNAKIDRLN | 0.83 | |
| 116 | BT_085 | AQVAKKVSAKIDQLN | 0.81 | |
| 117 | BT_086 | TQVAKKVNAKIDRLN | 0.82 | |
| 118 | BT_087 | AQVAKKVNAKIDQLN | 0.83 | |
| 119 | BT_088 | TQVAKKVNAKIDQLN | 0.84 | |
| 120 | BT_089 | TQVAKKVKAKIDQLN | 0.73 | |
| 121 | BT_090 | TQVAKKVTQKIDQLN | 0.71 | |
| 122 | BT_091 | KKVNAKIDRLNQIAS | 0.84 | |
| 123 | BT_092 | KKVNAKIDQLNQAAS | 0.84 | |
| 124 | BT_093 | KKVNAKIDQLNQIAS | 0.85 | |
| 125 | BT_094 | KKVNAKIDRLNQAAS | 0.83 | |
| 126 | BT_095 | KKVKAKIDQLNQAAS | 0.78 | |
| 127 | BT_096 | KKVNAKIDRLNQIAR | 0.84 | |
| 128 | BT_097 | KKVSAKIDQLNQAAS | 0.81 | |
| 129 | BT_098 | GVGQAAGFPLKRHDK | 0.87 | CagA_12/ |
| 130 | BT_099 | GVGQAAGFPLKKHDK | 0.84 | CagA_14 |
| 131 | BT_100 | GVGQAASFPLKKHGK | 0.77 | |
| 132 | BT_101 | GVGQAASFPLKRHDK | 0.81 | |
| 133 | BT_102 | GVGRAAGFPLKRHDK | 0.87 | |
| 134 | BT_103 | GVGQAVGFPLKRHDK | 0.87 | |
| 135 | BT_104 | GVGKAAGFPLKRHDK | 0.89 | |
| 136 | BT_105 | DVGQAANFLLKRHDK | 0.78 | |
| 137 | BT_106 | VVGQAVGFPLKRHDK | 0.89 | |
| 138 | BT_107 | GVGQAAGYPLKRHDK | 0.88 | |
| 139 | BT_108 | GVGQATGFPLKRHDK | 0.87 | |
| 140 | BT_109 | GVGQVAGFPLKKHGK | 0.77 | |
| 141 | BT_110 | VGQAGFPLKRHDKVD | 0.91 | |
| 142 | BT_111 | VGQAGFPLKRHDKVE | 0.92 | |
| 143 | BT_112 | VGQAGFPLKKHAKVE | 0.82 | |
| 144 | BT_113 | VNQAGFPLKRHDKVD | 0.91 | |
| 145 | BT_114 | VGQAGFLLKRHDKVD | 0.88 | |
| 146 | BT_115 | AGFPLKRHDKVDDLS | 0.91 | |
| 147 | BT_116 | GPFPLKRHDKVDDLS | 0.91 | |
| 148 | BT_117 | AGFPLKRHDKVEDLS | 0.91 | |
| 149 | BT_118 | AGFPLKKHDKVDDLS | 0.87 | |
| 150 | BT_119 | AGFPLKKHAKVEDLS | 0.87 | |
| 151 | BT_120 | AGFPLKKHDKVDDLS | 0.86 | |
| 152 | BT_121 | ASFPLKRHDKVDDLS | 0.90 | |
| 153 | BT_122 | EGFPLKRHDKVDDLS | 0.94 | |
| 154 | BT_123 | AGFPLKKHGKVDDLS | 0.86 | |
| 155 | BT_124 | AGFPLKKHGKVGDLS | 0.93 | |
| 156 | BT_125 | GSFPLKRHDKVEDLS | 0.92 | |
| 157 | BT_126 | AGYPLKRHDKVDDLS | 0.91 | |
| 158 | BT_127 | GSSPLKRHAKVDDLS | 0.78 | |
| 159 | BT_128 | TGFPLKKHDKVDDLS | 0.92 | |
| 160 | BT_129 | GPFPLKKHAKVDDLS | 0.84 | |
| 161 | BT_130 | LKRHDKVDDLSKVGL | 0.84 | |
| 162 | BT_131 | LKRHDKVDDLSKVGR | 0.83 | |
| 163 | BT_132 | LKRHDKVEDLSKVGR | 0.76 | |
| 164 | BT_133 | LKRHDKVEDLSKVGL | 0.70 | |
| 165 | BT_134 | LKRHDKVGDLSKVGL | 0.73 | |
| 166 | BT_135 | LKKHDKVEDLSKVGR | 0.71 | |
| 167 | BT_136 | LKKHDKVDDLSKVGR | 0.81 | |
| 168 | BT_137 | LKRHAKVDDLSKVGL | 0.79 | |
| 169 | BT_138 | LKKHDKVDDLSKVGL | 0.81 | |
| 170 | BT_139 | LKKHGKVDDLSKVGL | 0.74 | |
| 171 | BT_140 | RSVSPEPIYATIDDL | 0.84 | CagA_13 |
| 172 | BT_141 | LSASPEPIYATIDDL | 0.82 | |
| 173 | BT_142 | SASPEPIYATIDFDE | 0.72 | |
| 174 | BT_143 | LSANPEPIYATIDDL | 0.81 | |
| 175 | BT_144 | RLDSPEPIYATIDDL | 0.82 | |
| 176 | BT_145 | LSANHEPIYATIDDL | 0.77 | |
| 177 | BT_146 | NSDRSEPIYATIDDL | 0.74 | |
| 178 | BT_147 | LSASPEPIYATIDEL | 0.82 | |
| 179 | BT_148 | PEPIYATIDDLGGPF | 0.81 | |
| 180 | BT_149 | PEPIYATIDDLGGSF | 0.79 | |
| 181 | BT_150 | PEPIYATIDELGGPF | 0.77 | |
| 182 | BT_151 | SEPIYATIDDLGGPF | 0.76 | |
| 183 | BT_152 | HEPIYATIDDLDGPF | 0.74 | |
| 184 | BT_153 | HEPIYATIDDLGGPF | 0.74 | |
| 185 | BT_154 | EPIYATIDDLDGSSP | 0.74 | |
| 186 | BT_155 | IDDLGGPFPLKRHDK | 0.91 | CagA_14 |
| 187 | BT_156 | RHDKVDDLSKVGRSV | 0.70 | |
| 188 | BT_157 | DLNQAVSEAKIGHFD | 0.71 | CagA_15 |
| 189 | BT_158 | NGAINEKATGMLTQK | 0.76 | CagA_17 |
| 190 | BT_159 | NGTINEKATGMLTQK | 0.71 | |
| 191 | BT_160 | SGTINEKATGMLTQK | 0.70 | |
| 192 | BT_161 | TGTINEKATGMLTQK | 0.74 | |
| 193 | BT_162 | EKATGMLTQKNPEWL | 0.72 | |
| 194 | BT_163 | EKVTGMLTQKNPEWL | 0.72 | |
| 195 | BT_164 | LSEYDKIGFNQKNMK | 0.74 | CagA_18 |
| 196 | BT_165 | LSAYDKIGFNQKNMK | 0.78 | |
| 197 | BT_166 | LSDYDKIGFNQKNMK | 0.81 | |
| 198 | BT_167 | LSEYDNIGFNQKNMK | 0.76 | |
| 199 | BT_168 | LLEYDKIGFNQKNMK | 0.73 | |
| 200 | BT_169 | LSEYDKIGFSQKNMK | 0.74 | |
| 201 | BT_170 | LSEYDKIGFNQKSMK | 0.84 | |
| 202 | BT_171 | LSDYDKIGFNQKNMK | 0.78 | |
| 203 | BT_172 | KDYSDSFKFSTKLNN | 0.73 | |
| 204 | BT_173 | KDYSDSFKFSTKLSN | 0.71 | |
| 205 | BT_174 | KDYSDSFKFSTKLND | 0.72 | |
| 206 | BT_175 | KDYSDSFKFSTRLNN | 0.75 | |
| 207 | BT_176 | KDYSDSFKFSIKLSN | 0.72 | |

Example 6

Even a diagnostic with an ROC AUC of less than 0.7 may have a diagnostic capacity. In order to assess this, peptides to which a consistent fraction of CagA+ individuals had an antibody-response, but to which none of the individuals with a CagA-negative strain or lacking an *H. pylori* infection had such a response were identified. In this way 123 peptides with an ROC AUC of less than 0.7, for which the true-positive rate was more than 10% and the false-positive rate was 0%, were identified (Table 3). Each of these peptides can also be used for diagnosis of *H. pylori* CagA+ infection.

TABLE 3

| SEQ ID NO | Name | Sequence | AUC[1] | FPR[2] | TPR[3] | Epitope |
|---|---|---|---|---|---|---|
| 208 | BT_177 | NKSNDLINKDALIDV | 0.49 | 0 | 14 | CagA_01 |
| 209 | BT_178 | TTTDIQGLPPESRDL | 0.69 | 0 | 11 | CagA_03 |

TABLE 3-continued

| SEQ ID NO | Name | Sequence | AUC[1] | FPR[2] | TPR[3] | Epitope |
|---|---|---|---|---|---|---|
| 210 | BT_179 | STTHIQGLPPESRDL | 0.66 | 0 | 11 | |
| 211 | BT_180 | SFIFDKKQSSDVKEA | 0.55 | 0 | 11 | |
| 212 | BT_181 | SFVFDKKQSSDLKET | 0.54 | 0 | 11 | |
| 213 | BT_182 | SFAFDKKQSSDLKET | 0.53 | 0 | 11 | |
| 214 | BT_183 | ESRDLLDERGNFFKF | 0.66 | 0 | 14 | CagA_04 |
| 215 | BT_184 | EARDLLDERGDFSKF | 0.63 | 0 | 14 | |
| 216 | BT_185 | EARDLLDERGNFFKF | 0.62 | 0 | 14 | |
| 217 | BT_186 | LTPEARKLLEEAKKS | 0.52 | 0 | 14 | |
| 218 | BT_187 | NSQKDEIFALISKEA | 0.65 | 0 | 11 | CagA_05 |
| 219 | BT_188 | NSQKDEIFALINQET | 0.65 | 0 | 11 | |
| 220 | BT_189 | NSQKNEIFALINKEA | 0.64 | 0 | 11 | |
| 221 | BT_190 | NSQKDEIFKLINEGA | 0.57 | 0 | 11 | |
| 222 | BT_191 | NSQKDEILALINKEA | 0.52 | 0 | 11 | |
| 223 | BT_192 | VNKDLKDFSKSFDEF | 0.58 | 0 | 14 | CagA_06 |
| 224 | BT_193 | INKDLKDFSKSFDDF | 0.58 | 0 | 14 | |
| 225 | BT_194 | INKNLKDFSKSFDEF | 0.58 | 0 | 14 | |
| 226 | BT_195 | ISKDLKDFSKSFDEF | 0.56 | 0 | 14 | |
| 227 | BT_196 | KSFDGFKNGKNKDFS | 0.56 | 0 | 11 | |
| 228 | BT_197 | KIENLNVALNDFKNG | 0.55 | 0 | 11 | CagA_07 |
| 229 | BT_198 | EWISKIENLNVALND | 0.54 | 0 | 11 | |
| 230 | BT_199 | EWVSKVENLNAALNE | 0.53 | 0 | 11 | |
| 231 | BT_200 | EWISKVENLNAALND | 0.53 | 0 | 11 | |
| 232 | BT_201 | KVENLNAALNEFKNS | 0.52 | 0 | 11 | |
| 233 | BT_202 | KVENLNAALNEFKSG | 0.50 | 0 | 11 | |
| 234 | BT_203 | EWISKIENLNAALND | 0.49 | 0 | 11 | |
| 235 | BT_204 | IINQKITDKVGNLSS | 0.69 | 0 | 18 | CagA_08 |
| 236 | BT_205 | ITDKVDNLNQAVLVA | 0.67 | 0 | 18 | |
| 237 | BT_206 | KVDNLNQAVSEAKAT | 0.67 | 0 | 22 | |
| 238 | BT_207 | KVDNLNQAVSEAKLT | 0.66 | 0 | 14 | |
| 239 | BT_208 | VTDKVDNLNQAVSIA | 0.65 | 0 | 14 | |
| 240 | BT_209 | ITDKVDNLNQAVSMA | 0.64 | 0 | 11 | |
| 241 | BT_210 | VTDKVDNLNQEVSVA | 0.63 | 0 | 11 | |
| 242 | BT_211 | VTDKVDNLNQAVSMA | 0.62 | 0 | 14 | |
| 243 | BT_212 | ITDKVDNLNQAVSET | 0.62 | 0 | 11 | |
| 244 | BT_213 | VTDKVDNLNQAVSVA | 0.61 | 0 | 14 | |
| 245 | BT_214 | ITDKVDNLNQAVSVA | 0.61 | 0 | 11 | |
| 246 | BT_215 | KVDNLNQAVSIAKET | 0.59 | 0 | 25 | |
| 247 | BT_216 | KVDNLNQAVSVAKIT | 0.59 | 0 | 25 | |
| 248 | BT_217 | ITDKVDDLNQAVSVA | 0.59 | 0 | 11 | |
| 249 | BT_218 | KVDNLNQAVSIAKAT | 0.57 | 0 | 25 | |
| 250 | BT_219 | KVDNLSQAVSVAKIA | 0.56 | 0 | 11 | |
| 251 | BT_220 | KVDDLNQAVSVAKAT | 0.56 | 0 | 14 | |
| 252 | BT_221 | ITDKVDDLNQAVLVA | 0.56 | 0 | 11 | |
| 253 | BT_222 | ITNKVDDLNQAVSVA | 0.52 | 0 | 11 | |
| 254 | BT_223 | KVDNLSSAVSVAKAM | 0.52 | 0 | 11 | |
| 255 | BT_224 | VTDKVDDLNQAVSVA | 0.52 | 0 | 11 | |
| 256 | BT_225 | ITDKVDDLNQAVSMA | 0.50 | 0 | 11 | |
| 257 | BT_226 | TLSKNFSDIKKELNA | 0.68 | 0 | 22 | CagA_09 |
| 258 | BT_227 | TLTKKFSDIKKELNE | 0.68 | 0 | 18 | |
| 259 | BT_228 | NLTKNFSDIRKELNE | 0.67 | 0 | 11 | |
| 260 | BT_229 | TLTKNFSDIRKELNE | 0.66 | 0 | 14 | |
| 261 | BT_230 | NEKFKNFNNNNNGLK | 0.55 | 0 | 14 | |
| 262 | BT_231 | NSNGLKNSAEPIYAQ | 0.62 | 0 | 11 | CagA_10 |
| 263 | BT_232 | NNNGLKNSTEPIYAK | 0.60 | 0 | 11 | |
| 264 | BT_233 | TQVAKKVKAKIDRLD | 0.67 | 0 | 11 | CagA_11 |
| 265 | BT_234 | TQVAKKVTKKIDQLN | 0.61 | 0 | 11 | |
| 266 | BT_235 | RHDKVDDLSKIGRSV | 0.69 | 0 | 14 | CagA_12 |
| 267 | BT_236 | RHDKVDDLSKVGLSR | 0.69 | 0 | 22 | |
| 268 | BT_237 | KHAKVDDLSKVGRSV | 0.68 | 0 | 14 | |
| 269 | BT_238 | RHDKVDDLSKVGLSA | 0.68 | 0 | 18 | |
| 270 | BT_239 | LKRYAKVDDLSKVGL | 0.68 | 0 | 25 | |
| 271 | BT_240 | RHDKVDDLSKVGRSR | 0.66 | 0 | 18 | |
| 272 | BT_241 | LKRYAKVDDLSKAGR | 0.66 | 0 | 22 | |
| 273 | BT_242 | RYAKVDDLSKVGLSR | 0.63 | 0 | 18 | |
| 274 | BT_243 | KVDDLSKVGLSANHE | 0.62 | 0 | 14 | |
| 275 | BT_244 | KVDDLSKVGLSREQE | 0.60 | 0 | 14 | |
| 276 | BT_245 | KVDDLTKVGFSREQE | 0.60 | 0 | 11 | |

TABLE 3-continued

| SEQ ID NO | Name | Sequence | AUC[1] | FPR[2] | TPR[3] | Epitope |
|---|---|---|---|---|---|---|
| 277 | BT_246 | KVDDLSKVGLSANPE | 0.60 | 0 | 14 | |
| 278 | BT_247 | VGQAGFPFKKHAKVE | 0.59 | 0 | 11 | |
| 279 | BT_248 | GSSPLKRYAKVDDLS | 0.56 | 0 | 11 | |
| 280 | BT_249 | PEPIYATIDFDDANQ | 0.68 | 0 | 18 | CagA_13 |
| 281 | BT_250 | PEPIYATIDFDEANQ | 0.61 | 0 | 18 | |
| 282 | BT_251 | AVSEAKAGFFGNLEQ | 0.66 | 0 | 14 | CagA_15 |
| 283 | BT_252 | KAGFFGNLEQTIDKL | 0.64 | 0 | 18 | |
| 284 | BT_253 | AVSEAKAGFFGNLER | 0.64 | 0 | 14 | |
| 285 | BT_254 | KAGFFGNLEQTIGNL | 0.64 | 0 | 18 | |
| 286 | BT_255 | KVGFFGNLEQTIDKL | 0.63 | 0 | 11 | |
| 287 | BT_256 | AVSEAKVGFFGNLEQ | 0.63 | 0 | 11 | |
| 288 | BT_257 | KAGFFGNLEQTIDNL | 0.63 | 0 | 22 | |
| 289 | BT_258 | KAGFFGNLEQTINNL | 0.63 | 0 | 14 | |
| 290 | BT_259 | KAGYFGNLEQTIDNL | 0.63 | 0 | 14 | |
| 291 | BT_260 | KAGFFGNLERTIDKL | 0.62 | 0 | 25 | |
| 292 | BT_261 | AVSEAKSGFFGNLEQ | 0.62 | 0 | 14 | |
| 293 | BT_262 | KAGFFGNLEQTMDRL | 0.61 | 0 | 18 | |
| 294 | BT_263 | KAGYFGNLEQTIDKL | 0.61 | 0 | 25 | |
| 295 | BT_264 | KAGFFGNLERTIDNL | 0.61 | 0 | 18 | |
| 296 | BT_265 | AVSEAKAGYFGNLEQ | 0.54 | 0 | 14 | |
| 297 | BT_266 | KVPDSLSAKLDNYAT | 0.62 | 0 | 14 | CagA_16 |
| 298 | BT_267 | MNLWAESAKKVPAGL | 0.58 | 0 | 11 | |
| 299 | BT_268 | VNLWAESAKKVPVSL | 0.57 | 0 | 14 | |
| 300 | BT_269 | KVPASLLEKLDNYAT | 0.56 | 0 | 18 | |
| 301 | BT_270 | MNLWAESAKKVPASL | 0.55 | 0 | 11 | |
| 302 | BT_271 | VNLWAENAKKLPASL | 0.54 | 0 | 11 | |
| 303 | BT_272 | VESAKQVPAGLQAKL | 0.48 | 0 | 11 | |
| 304 | BT_273 | NGGINEKATGMLTQK | 0.69 | 0 | 14 | CagA_17 |
| 305 | BT_274 | EKAIGMLTQKNPEWL | 0.66 | 0 | 11 | |
| 306 | BT_275 | EKATGVLTQKNPEWL | 0.63 | 0 | 11 | |
| 307 | BT_276 | EKATGMLMQKNPEWL | 0.58 | 0 | 11 | |
| 308 | BT_277 | KDYSDSFKFSTKLNS | 0.69 | 0 | 37 | CagA_18 |
| 309 | BT_278 | GSVPLSAYDKIGFNQ | 0.69 | 0 | 18 | |
| 310 | BT_279 | GSVSLSEYDKIGFNQ | 0.69 | 0 | 22 | |
| 311 | BT_280 | GSTHLSEYDKIGFNQ | 0.67 | 0 | 18 | |
| 312 | BT_281 | LSEYDNIGFSQKNMK | 0.65 | 0 | 11 | |
| 313 | BT_282 | GSAHLSEYDKIGFNQ | 0.64 | 0 | 18 | |
| 314 | BT_283 | GSAPLSDYDKIGFNQ | 0.64 | 0 | 18 | |
| 315 | BT_284 | DSFKFSTKLNSAIKD | 0.64 | 0 | 18 | |
| 316 | BT_285 | GSVPLSEYDKIGFNQ | 0.64 | 0 | 22 | |
| 317 | BT_286 | GSAPLSEYDNIGFSQ | 0.63 | 0 | 11 | |
| 318 | BT_287 | GSAPLSEYDKIGFNQ | 0.62 | 0 | 22 | |
| 319 | BT_288 | GSAPLSAYDKIGFNQ | 0.62 | 0 | 22 | |
| 320 | BT_289 | DSFKFSTKLNDAVKD | 0.62 | 0 | 18 | |
| 321 | BT_290 | DSFKFSTKLNNAVKN | 0.61 | 0 | 14 | |
| 322 | BT_291 | GSVPLSEYDNIGFNQ | 0.61 | 0 | 22 | |
| 323 | BT_292 | DSFKFSTKLNNAVKD | 0.61 | 0 | 14 | |
| 324 | BT_293 | DSFKFSTKLSNAVKN | 0.61 | 0 | 11 | |
| 325 | BT_294 | DSFKFSTRLNNAVKD | 0.60 | 0 | 11 | |
| 326 | BT_295 | GSTPLSDYDKIGFNQ | 0.60 | 0 | 22 | |
| 327 | BT_296 | DSFKFSTELNNAVKD | 0.60 | 0 | 11 | |
| 328 | BT_297 | GSTPLSEYDKIGFNQ | 0.59 | 0 | 22 | |
| 329 | BT_298 | DSFKFSTKLSNAVKD | 0.57 | 0 | 11 | |
| 330 | BT_299 | DSFKFSTKSNNAVKD | 0.55 | 0 | 14 | |

[1]AUC - Area under the curve for the Receiver Operating Characteristic (ROC) curve.
[2]FPR - False-positive rate (%) based on a cut-off set to the 95th percentile of all the peptides tested (n = 1144 peptides).
[3]TPR - True-positive rate (%) based on a cut-off set to the 95th percentile of all the peptides tested (n = 1144 peptides).

Example 7—Identification of Crucial Amino-Acid Sequences for Diagnosing a CagA+ *H. pylori* Infection A detailed mapping of B-cell epitopes of *H. pylori* CagA within peptides identified as highly diagnostic was performed. Mapping was performed using high-density peptide arrays. Individual serum samples (n=48) were tested for antibody-binding to sequence variants of each of the selected peptides. This was done in order to pin-point amino acid positions in each peptide that contributed to antibody-binding, and therefore would be crucial to include in a diagnostic application.

We selected the peptides with the highest diagnostic potential, and for each of the selected peptides we created 300 different sequence variants. This was done by so called complete single-residue substitution. This means that for each of the 15 amino-acid positions of each peptide, we created 20 different sequence variants that only differed in sequence in that position; in that position, the 20 variants had one each of the 20 different common protein amino acids. Since there were 20 different sequence variants per amino acid position, and the peptides were of 15 amino acids length, there were in total 300 different sequence variants. The procedure has been described previously (Hansen et al, PLOS One 2013:8 (7):e68902). This analysis determined if a given residue position within the peptide is unimportant for binding of the peptide to the antibody, i.e. if the amino acid residues in the native sequence can be freely substituted without affecting binding.

In this way all variants of the selected peptides were tested for antibody-binding by each of the 48 serum samples. We observed which peptide variants obtained significantly/substantially lower ROC AUC-scores than the original peptide, and based on this information we could identify the sequence motifs that were crucial for discriminatory capacity of CagA+ *H. pylori* infection.

Figure 3:
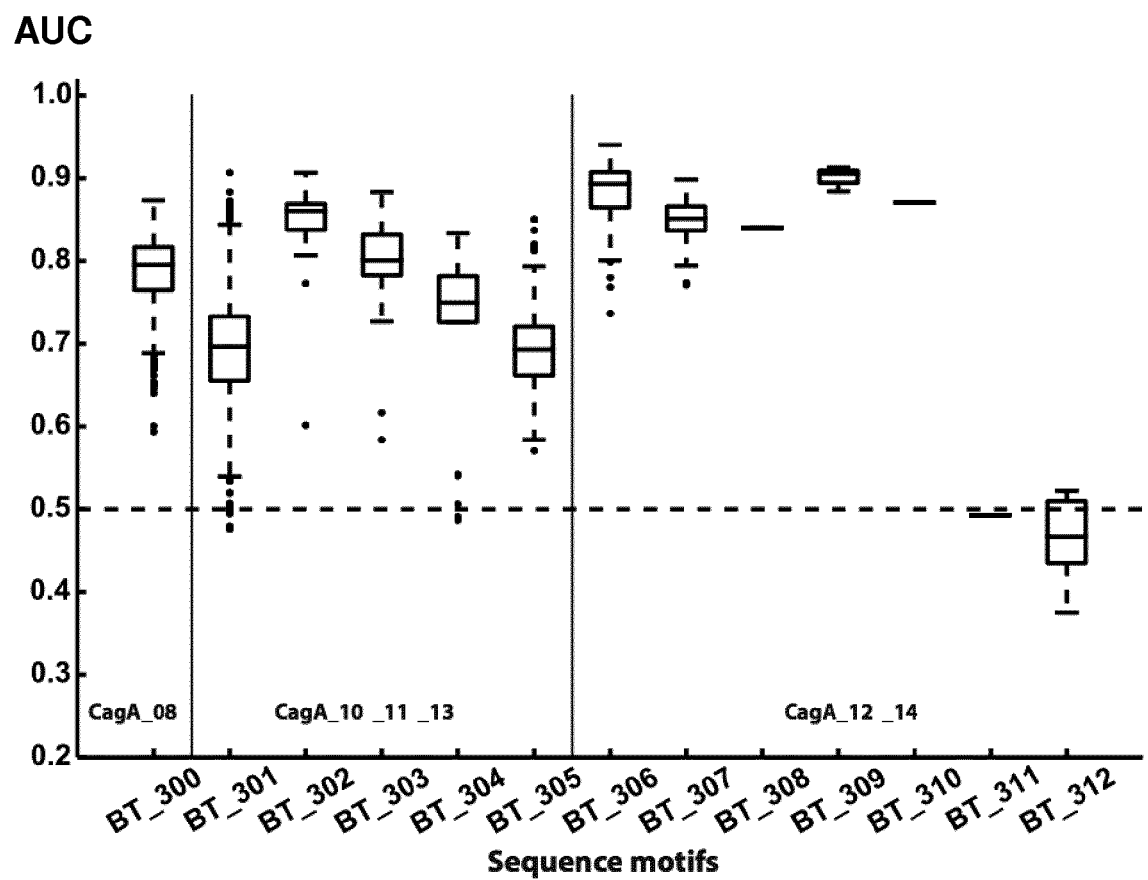
FIG. 3 ROC AUC scores for all peptides containing crucial sequence motifs. Data are shown as median, interquartile range and outliers. If only one peptide was tested, only the median is shown (horizontal line). The sequence motif designations are identical to the sequence names of Table 4.

It was revealed that the crucial parts of the peptides span between 5-6 amino acids, and that there is redundancy in some of the positions of these crucial sequences. The crucial sequences for certain epitopes are shown in Table 4, and their ROC AUC levels in FIG. 3. The peptides of table 4 are particularly useful for diagnosis and treatment of *H. pylori* infection and gastric cancer, including prevention of cancer, since they are highly specific.

TABLE 4

| SEQ ID NO | Name | Sequence[1] | AUC[2] | n[3] | Epitope(s) |
|---|---|---|---|---|---|
| 13 | BT_300 | IINQKVTDKVDNLNQ[4] | 0.80 (0.77-0.82) | 298 | CagA_08 |
| 8 | BT_301 | EPIYA | 0.70 (0.66-0.73) | 283 | CagA_10_11_13 |
| 9 | BT_302 | EPIYAK | 0.86 (0.84-0.87) | 16 | CagA_10 |
| 10 | BT_303 | EPIYAQ | 0.80 (0.78-0.83) | 21 | CagA_10_11 |
| 11 | BT_304 | EPIYT | 0.75 (0.73-0.78) | 21 | CagA_11 |
| 12 | BT_305 | EPIYAT | 0.70 (0.66-0.72) | 211 | CagA_13 |
| 1 | BT_306 | FXLKRHX | 0.90 (0.87-0.91) | 275 | CagA_12_14 |
| 2 | BT_307 | FXLKKHX | 0.85 (0.84-0.87) | 34 | |
| 3 | BT_308 | FXLKQHX | 0.84 | N.A. | 1 | |
| 4 | BT_309 | YXLKRHX | 0.91 (0.89-0.91) | 3 | |
| 5 | BT_310 | IXLKRHX | 0.87 | N.A. | 1 | |
| 6 | BT_311 | FXLRRYX | 0.49 | N.A. | 1 | |
| 7 | BT_312 | FXLRRSX | 0.47 (0.44-0.51) | 7 | |

[1]An "X" means any one amino acid as described herein.
[2]AUC is expressed as median, with interquartile range in brackets (N.A = not applicable).
[3]Number of different 15-mer peptide sequences tested.
[4]The AUC data of Seq ID NO 13 includes sequence variants of sequence 13. The data includes all peptides with an exact match in at least 12 out of the 15 amino acids.

The invention claimed is:

1. A method of diagnosis comprising the steps of:
   a) providing a sample from a subject having, or suspected of having, a *Helicobacter pylori* infection and/or increased risk of gastric cancer in the subject,
   b) contacting said sample with a peptide comprising an amino acid sequence selected from the group consisting of: SEQ ID NO:2, SEQ ID NO:3, SEQ ID NO:4, SEQ ID NO:5, SEQ ID NO:6, and SEQ ID NO:7, said peptide comprising at most 25 amino acids, or a peptide consisting of SEQ ID NO:1,
   c) detecting specific binding of antibodies in the sample to the peptide, wherein presence of antibodies in the sample which specifically bind to the peptide is indicative of *Helicobacter pylori* infection and/or increased risk of gastric cancer in the subject.

2. The method according to claim 1 where the peptide is selected from the group consisting of: SEQ ID NO:2, SEQ ID NO:3, SEQ ID NO:4, and SEQ ID NO:5.

3. A method for treating a *Helicobacter pylori* infection in a subject comprising using the diagnosis method of claim to determine that the subject has a *Helicobacter pylori* infection, and then treating the infection.

4. The method of claim 3 where the treatment involves administering at least two antibiotics selected from the group consisting of macrolides, beta-lactams, nitroimidazoles, tetracyclines and fluoroquinolones.

5. The method of claim 4 where the treatment involves administration of a proton pump inhibitor to the subject.

6. The method of claim 1, wherein the peptide is selected from the group consisting of: SEQ ID NO:2, SEQ ID NO:3, SEQ ID NO:4, SEQ ID NO:5, SEQ ID NO:6, and SEQ ID NO:7 and wherein the peptide comprises at most twenty-five amino acids.

7. The method of claim 1, wherein the peptide is selected from the group consisting of: SEQ ID NO:2, SEQ ID NO:3, SEQ ID NO:4, SEQ ID NO:5, SEQ ID NO:6, and SEQ ID NO:7, and wherein the peptide comprises at most ten amino acids.

8. The method of claim 1, wherein the sample is a blood, serum, plasma or gastric tissue sample.

* * * * *

SEQUENCE LISTING

<160> NUMBER OF SEQ ID NOS: 332

<210> SEQ ID NO 1
<211> LENGTH: 7
<212> TYPE: PRT
<213> ORGANISM: Helicobacter pylori
<220> FEATURE:
<221> NAME/KEY: VARIANT
<222> LOCATION: 2
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is any amino acid

<400> SEQUENCE: 1

Phe Xaa Leu Lys Arg His Xaa
1               5

<210> SEQ ID NO 2
<211> LENGTH: 7
<212> TYPE: PRT
<213> ORGANISM: Helicobacter pylori
<220> FEATURE:
<223> OTHER INFORMATION: 325
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is any amino acid

<400> SEQUENCE: 2

Phe Xaa Leu Lys Lys His Xaa 1               5

<210> SEQ ID NO 3
<211> LENGTH: 7
<212> TYPE: PRT
<213> ORGANISM: Helicobacter pylori
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is any amino acid

<400> SEQUENCE: 3

Phe Xaa Leu Lys Gln His Xaa
1               5

<210> SEQ ID NO 4
<211> LENGTH: 7
<212> TYPE: PRT
<213> ORGANISM: Helicobacter pylori
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is any amino acid

<400> SEQUENCE: 4

Tyr Xaa Leu Lys Arg His Xaa
1               5

<210> SEQ ID NO 5
<211> LENGTH: 7
<212> TYPE: PRT
<213> ORGANISM: Helicobacter pylori
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is any amino acid

<400> SEQUENCE: 5

Ile Xaa Leu Lys Arg His Xaa
1               5

<210> SEQ ID NO 6
<211> LENGTH: 7
<212> TYPE: PRT
<213> ORGANISM: Helicobacter pylori
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is any amino acid

<400> SEQUENCE: 6

Phe Xaa Leu Arg Arg Tyr Xaa
1               5

```
<210> SEQ ID NO 7
<211> LENGTH: 7
<212> TYPE: PRT
<213> ORGANISM: Helicobacter pylori
<220> FEATURE:
<221> NAME/KEY: VARIANT
<222> LOCATION: 2
<223> OTHER INFORMATION: Xaa is any amio acid
<220> FEATURE:
<221> NAME/KEY: VARIANT
<222> LOCATION: 7
<223> OTHER INFORMATION: Xaa is any amino acid

<400> SEQUENCE: 7

Phe Xaa Leu Arg Arg Ser Xaa
1               5

<210> SEQ ID NO 8
<211> LENGTH: 5
<212> TYPE: PRT
<213> ORGANISM: Helicobacter pylori

<400> SEQUENCE: 8

Glu Pro Ile Tyr Ala
1               5

<210> SEQ ID NO 9
<211> LENGTH: 6
<212> TYPE: PRT
<213> ORGANISM: Helicobacter pylori

<400> SEQUENCE: 9

Glu Pro Ile Tyr Ala Lys
1               5

<210> SEQ ID NO 10
<211> LENGTH: 6
<212> TYPE: PRT
<213> ORGANISM: Helicobacter pylori

<400> SEQUENCE: 10

Glu Pro Ile Tyr Ala Gln
1               5

<210> SEQ ID NO 11
<211> LENGTH: 5
<212> TYPE: PRT
<213> ORGANISM: Helicobacter pylori

<400> SEQUENCE: 11

Glu Pro Ile Tyr Thr
1               5

<210> SEQ ID NO 12
<211> LENGTH: 6
<212> TYPE: PRT
<213> ORGANISM: Helicobacter pylori

<400> SEQUENCE: 12

Glu Pro Ile Tyr Ala Thr
1               5

<210> SEQ ID NO 13
<211> LENGTH: 15
<212> TYPE: PRT
<213> ORGANISM: Helicobacter pylori
```

```
<400> SEQUENCE: 13

Ile Ile Asn Gln Lys Val Thr Asp Lys Val Asp Asn Leu Asn Gln
1               5                   10                  15

<210> SEQ ID NO 14
<211> LENGTH: 31
<212> TYPE: PRT
<213> ORGANISM: Helicobacter pylori

<400> SEQUENCE: 14

Asn Pro Thr Lys Lys Asn Gln Tyr Phe Ser Asp Phe Ile Asp Lys Ser
1               5                   10                  15

Asn Asp Leu Ile Asn Lys Asp Asn Leu Ile Asp Val Glu Ser Ser
            20                  25                  30

<210> SEQ ID NO 15
<211> LENGTH: 25
<212> TYPE: PRT
<213> ORGANISM: Helicobacter pylori

<400> SEQUENCE: 15

Asp Pro Ser Lys Ile Asn Thr Arg Ser Ile Arg Asn Phe Met Glu Asn
1               5                   10                  15

Ile Ile Gln Pro Pro Ile Pro Asp Asp
            20                  25

<210> SEQ ID NO 16
<211> LENGTH: 33
<212> TYPE: PRT
<213> ORGANISM: Helicobacter pylori

<400> SEQUENCE: 16

Lys Lys Gln Ser Ser Asp Val Lys Glu Ala Ile Asn Gln Glu Pro Val
1               5                   10                  15

Pro His Val Gln Pro Asp Ile Ala Thr Thr Thr Thr Asp Ile Gln Gly
            20                  25                  30

Leu

<210> SEQ ID NO 17
<211> LENGTH: 31
<212> TYPE: PRT
<213> ORGANISM: Helicobacter pylori

<400> SEQUENCE: 17

Pro Glu Ala Arg Asp Leu Leu Asp Glu Arg Gly Asn Phe Ser Lys Phe
1               5                   10                  15

Thr Leu Gly Asp Met Glu Met Leu Asp Val Glu Gly Val Ala Asp
            20                  25                  30

<210> SEQ ID NO 18
<211> LENGTH: 22
<212> TYPE: PRT
<213> ORGANISM: Helicobacter pylori

<400> SEQUENCE: 18

Lys Ala Gln Ala Asn Ser Gln Lys Asp Glu Ile Phe Ala Leu Ile Asn
1               5                   10                  15

Lys Glu Ala Asn Arg Asp
            20

<210> SEQ ID NO 19
```

-continued

<211> LENGTH: 24
<212> TYPE: PRT
<213> ORGANISM: Helicobacter pylori

<400> SEQUENCE: 19

Ser Lys Asp Leu Lys Asp Phe Ser Lys Ser Phe Asp Glu Phe Lys Asn
1               5                   10                  15

Gly Lys Asn Lys Asp Phe Ser Lys
            20

<210> SEQ ID NO 20
<211> LENGTH: 24
<212> TYPE: PRT
<213> ORGANISM: Helicobacter pylori

<400> SEQUENCE: 20

Gly Ile Asn Pro Glu Trp Ile Ser Lys Val Glu Asn Leu Asn Ala Ala
1               5                   10                  15

Leu Asn Glu Phe Lys Asn Gly Lys
            20

<210> SEQ ID NO 21
<211> LENGTH: 17
<212> TYPE: PRT
<213> ORGANISM: Helicobacter pylori

<400> SEQUENCE: 21

Ile Asn Gln Lys Val Thr Asp Lys Val Asp Asn Leu Asn Gln Ala Val
1               5                   10                  15

Ser

<210> SEQ ID NO 22
<211> LENGTH: 20
<212> TYPE: PRT
<213> ORGANISM: Helicobacter pylori

<400> SEQUENCE: 22

Phe Ser Asp Ile Lys Lys Glu Leu Asn Glu Lys Phe Lys Asn Phe Asn
1               5                   10                  15

Asn Asn Asn Asn
            20

<210> SEQ ID NO 23
<211> LENGTH: 17
<212> TYPE: PRT
<213> ORGANISM: Helicobacter pylori

<400> SEQUENCE: 23

Lys Asn Ser Thr Glu Pro Ile Tyr Ala Lys Val Asn Lys Lys Lys Thr
1               5                   10                  15

Gly

<210> SEQ ID NO 24
<211> LENGTH: 20
<212> TYPE: PRT
<213> ORGANISM: Helicobacter pylori

<400> SEQUENCE: 24

Tyr Thr Gln Val Ala Lys Lys Val Asn Ala Lys Ile Asp Arg Leu Asn
1               5                   10                  15

Gln Ile Ala Ser
            20

<210> SEQ ID NO 25
<211> LENGTH: 17
<212> TYPE: PRT
<213> ORGANISM: Helicobacter pylori

<400> SEQUENCE: 25

Ala Ala Gly Phe Pro Leu Lys Arg His Asp Lys Val Asp Asp Leu Ser
1               5                   10                  15

Lys

<210> SEQ ID NO 26
<211> LENGTH: 15
<212> TYPE: PRT
<213> ORGANISM: Helicobacter pylori

<400> SEQUENCE: 26

Gly Leu Ser Ala Ser Pro Glu Pro Ile Tyr Ala Thr Ile Asp Asp
1               5                   10                  15

<210> SEQ ID NO 27
<211> LENGTH: 17
<212> TYPE: PRT
<213> ORGANISM: Helicobacter pylori

<400> SEQUENCE: 27

Gly Gly Pro Phe Pro Leu Lys Arg His Asp Lys Val Asp Asp Leu Ser
1               5                   10                  15

Lys

<210> SEQ ID NO 28
<211> LENGTH: 17
<212> TYPE: PRT
<213> ORGANISM: Helicobacter pylori

<400> SEQUENCE: 28

Val Ser Glu Ala Lys Ala Gly Phe Phe Gly Asn Leu Glu Gln Thr Ile
1               5                   10                  15

Asp

<210> SEQ ID NO 29
<211> LENGTH: 18
<212> TYPE: PRT
<213> ORGANISM: Helicobacter pylori

<400> SEQUENCE: 29

Glu Ser Ala Lys Lys Val Pro Ala Ser Leu Ser Ala Lys Leu Asp Asn
1               5                   10                  15

Tyr Ala

<210> SEQ ID NO 30
<211> LENGTH: 18
<212> TYPE: PRT
<213> ORGANISM: Helicobacter pylori

<400> SEQUENCE: 30

Gly Ala Ile Asn Glu Lys Ala Thr Gly Met Leu Thr Gln Lys Asn Pro
1               5                   10                  15

Glu Trp

<210> SEQ ID NO 31

```
<211> LENGTH: 27
<212> TYPE: PRT
<213> ORGANISM: Helicobacter pylori

<400> SEQUENCE: 31

Ser Glu Tyr Asp Lys Ile Gly Phe Asn Gln Lys Asn Met Lys Asp Tyr
1               5                   10                  15

Ser Asp Ser Phe Lys Phe Ser Thr Lys Leu Asn
            20                  25

<210> SEQ ID NO 32
<211> LENGTH: 15
<212> TYPE: PRT
<213> ORGANISM: Helicobacter pylori

<400> SEQUENCE: 32

Asp Val Lys Glu Ala Ile Asn Gln Glu Pro Val Pro His Val Gln
1               5                   10                  15

<210> SEQ ID NO 33
<211> LENGTH: 15
<212> TYPE: PRT
<213> ORGANISM: Helicobacter pylori

<400> SEQUENCE: 33

Asp Val Lys Glu Ala Ile Asn Gln Glu Pro Leu Pro His Val Gln
1               5                   10                  15

<210> SEQ ID NO 34
<211> LENGTH: 15
<212> TYPE: PRT
<213> ORGANISM: Helicobacter pylori

<400> SEQUENCE: 34

Asp Val Lys Glu Ala Ile Asn Gln Glu Pro Val Pro His Ile Gln
1               5                   10                  15

<210> SEQ ID NO 35
<211> LENGTH: 15
<212> TYPE: PRT
<213> ORGANISM: Helicobacter pylori

<400> SEQUENCE: 35

Asp Val Lys Glu Ala Ile Asn Gln Glu Pro Val Pro Asn Val Gln
1               5                   10                  15

<210> SEQ ID NO 36
<211> LENGTH: 15
<212> TYPE: PRT
<213> ORGANISM: Helicobacter pylori

<400> SEQUENCE: 36

Thr Thr Thr His Ile Gln Gly Leu Pro Pro Glu Ser Arg Asp Leu
1               5                   10                  15

<210> SEQ ID NO 37
<211> LENGTH: 15
<212> TYPE: PRT
<213> ORGANISM: Helicobacter pylori

<400> SEQUENCE: 37

Thr Thr Thr Pro Ile Gln Gly Leu Pro Pro Glu Ser Arg Asp Leu
1               5                   10                  15
```

```
<210> SEQ ID NO 38
<211> LENGTH: 15
<212> TYPE: PRT
<213> ORGANISM: Helicobacter pylori

<400> SEQUENCE: 38

Thr Pro Thr His Ile Gln Gly Leu Pro Pro Glu Ala Arg Asp Leu
1               5                   10                  15

<210> SEQ ID NO 39
<211> LENGTH: 15
<212> TYPE: PRT
<213> ORGANISM: Helicobacter pylori

<400> SEQUENCE: 39

Gln Gly Leu Pro Pro Glu Ser Arg Asp Leu Leu Asp Glu Arg Gly
1               5                   10                  15

<210> SEQ ID NO 40
<211> LENGTH: 15
<212> TYPE: PRT
<213> ORGANISM: Helicobacter pylori

<400> SEQUENCE: 40

Gln Gly Leu Pro Pro Glu Ala Arg Asp Leu Leu Asp Glu Arg Gly
1               5                   10                  15

<210> SEQ ID NO 41
<211> LENGTH: 15
<212> TYPE: PRT
<213> ORGANISM: Helicobacter pylori

<400> SEQUENCE: 41

Gln Ser Leu Pro Pro Glu Ala Arg Asp Leu Leu Asp Glu Arg Gly
1               5                   10                  15

<210> SEQ ID NO 42
<211> LENGTH: 15
<212> TYPE: PRT
<213> ORGANISM: Helicobacter pylori

<400> SEQUENCE: 42

Gln Gly Leu Pro Leu Glu Ala Arg Asp Leu Leu Asp Glu Arg Gly
1               5                   10                  15

<210> SEQ ID NO 43
<211> LENGTH: 15
<212> TYPE: PRT
<213> ORGANISM: Helicobacter pylori

<400> SEQUENCE: 43

Glu Ser Arg Asp Leu Leu Asp Glu Arg Gly Asn Phe Ser Lys Phe
1               5                   10                  15

<210> SEQ ID NO 44
<211> LENGTH: 15
<212> TYPE: PRT
<213> ORGANISM: Helicobacter pylori

<400> SEQUENCE: 44

Leu Asp Glu Arg Gly Asn Phe Phe Lys Phe Thr Leu Gly Asp Met
1               5                   10                  15

<210> SEQ ID NO 45
<211> LENGTH: 15
```

<212> TYPE: PRT
<213> ORGANISM: Helicobacter pylori

<400> SEQUENCE: 45

Asn Phe Ser Lys Phe Thr Leu Gly Asp Met Glu Met Leu Asp Val
1               5                   10                  15

<210> SEQ ID NO 46
<211> LENGTH: 15
<212> TYPE: PRT
<213> ORGANISM: Helicobacter pylori

<400> SEQUENCE: 46

Asn Phe Phe Lys Phe Thr Leu Gly Asp Val Glu Met Leu Asp Val
1               5                   10                  15

<210> SEQ ID NO 47
<211> LENGTH: 15
<212> TYPE: PRT
<213> ORGANISM: Helicobacter pylori

<400> SEQUENCE: 47

Asn Phe Ser Lys Phe Thr Leu Gly Asp Met Asn Met Leu Asp Val
1               5                   10                  15

<210> SEQ ID NO 48
<211> LENGTH: 15
<212> TYPE: PRT
<213> ORGANISM: Helicobacter pylori

<400> SEQUENCE: 48

Asp Phe Ser Lys Phe Thr Leu Gly Asp Met Glu Met Leu Asp Val
1               5                   10                  15

<210> SEQ ID NO 49
<211> LENGTH: 15
<212> TYPE: PRT
<213> ORGANISM: Helicobacter pylori

<400> SEQUENCE: 49

Asn Phe Phe Lys Phe Thr Leu Gly Asp Met Glu Met Leu Asp Val
1               5                   10                  15

<210> SEQ ID NO 50
<211> LENGTH: 15
<212> TYPE: PRT
<213> ORGANISM: Helicobacter pylori

<400> SEQUENCE: 50

Asn Phe Pro Lys Phe Thr Leu Gly Asp Met Glu Met Leu Asp Val
1               5                   10                  15

<210> SEQ ID NO 51
<211> LENGTH: 15
<212> TYPE: PRT
<213> ORGANISM: Helicobacter pylori

<400> SEQUENCE: 51

Asn Phe Ser Lys Phe Thr Leu Gly Asp Val Glu Met Leu Asp Val
1               5                   10                  15

<210> SEQ ID NO 52
<211> LENGTH: 15
<212> TYPE: PRT
<213> ORGANISM: Helicobacter pylori

<400> SEQUENCE: 52

Ile Lys Asp Val Ile Ile Asn Gln Glu Ile Thr Asp Lys Val Asp
1               5                   10                  15

<210> SEQ ID NO 53
<211> LENGTH: 15
<212> TYPE: PRT
<213> ORGANISM: Helicobacter pylori

<400> SEQUENCE: 53

Ile Ile Asn Gln Lys Ile Thr Asp Lys Val Asp Asn Leu Asn Gln
1               5                   10                  15

<210> SEQ ID NO 54
<211> LENGTH: 15
<212> TYPE: PRT
<213> ORGANISM: Helicobacter pylori

<400> SEQUENCE: 54

Ile Ile Asn Gln Lys Val Thr Asp Lys Val Asp Asn Leu Asn Gln
1               5                   10                  15

<210> SEQ ID NO 55
<211> LENGTH: 15
<212> TYPE: PRT
<213> ORGANISM: Helicobacter pylori

<400> SEQUENCE: 55

Ile Ile Asn Gln Lys Ile Thr Asp Lys Val Asp Asp Leu Asn Gln
1               5                   10                  15

<210> SEQ ID NO 56
<211> LENGTH: 15
<212> TYPE: PRT
<213> ORGANISM: Helicobacter pylori

<400> SEQUENCE: 56

Ile Ile Asn Gln Lys Ile Thr Asp Lys Val Asp Asn Leu Ser Gln
1               5                   10                  15

<210> SEQ ID NO 57
<211> LENGTH: 15
<212> TYPE: PRT
<213> ORGANISM: Helicobacter pylori

<400> SEQUENCE: 57

Ile Ile Asn Gln Lys Ile Thr Asp Lys Val Asp Asn Leu Ser Ser
1               5                   10                  15

<210> SEQ ID NO 58
<211> LENGTH: 15
<212> TYPE: PRT
<213> ORGANISM: Helicobacter pylori

<400> SEQUENCE: 58

Ile Ile Asn Gln Lys Val Thr Asp Lys Val Asp Asp Leu Asn Gln
1               5                   10                  15

<210> SEQ ID NO 59
<211> LENGTH: 15
<212> TYPE: PRT
<213> ORGANISM: Helicobacter pylori

<400> SEQUENCE: 59

Ile Ile Asn Gln Glu Ile Thr Asp Lys Val Asp Leu Asn Gln
1               5                   10                  15

<210> SEQ ID NO 60
<211> LENGTH: 15
<212> TYPE: PRT
<213> ORGANISM: Helicobacter pylori

<400> SEQUENCE: 60

Ile Ile Asn Gln Lys Ile Thr Asp Lys Ala Asp Asn Leu Asn Gln
1               5                   10                  15

<210> SEQ ID NO 61
<211> LENGTH: 15
<212> TYPE: PRT
<213> ORGANISM: Helicobacter pylori

<400> SEQUENCE: 61

Ile Ile Asn Gln Lys Val Thr Asp Lys Val Asp Asn Leu Ser Ser
1               5                   10                  15

<210> SEQ ID NO 62
<211> LENGTH: 15
<212> TYPE: PRT
<213> ORGANISM: Helicobacter pylori

<400> SEQUENCE: 62

Ile Ile Asn Gln Lys Ile Thr Asp Lys Val Asp Ser Leu Asn Gln
1               5                   10                  15

<210> SEQ ID NO 63
<211> LENGTH: 15
<212> TYPE: PRT
<213> ORGANISM: Helicobacter pylori

<400> SEQUENCE: 63

Ile Ile Asn Gln Lys Ile Thr Asp Lys Val Glu Asn Leu Asn Gln
1               5                   10                  15

<210> SEQ ID NO 64
<211> LENGTH: 15
<212> TYPE: PRT
<213> ORGANISM: Helicobacter pylori

<400> SEQUENCE: 64

His Ile Asn Gln Gln Ile Thr Asp Lys Val Asp Asn Leu Asn Gln
1               5                   10                  15

<210> SEQ ID NO 65
<211> LENGTH: 15
<212> TYPE: PRT
<213> ORGANISM: Helicobacter pylori

<400> SEQUENCE: 65

Ile Phe Asn Gln Lys Ile Thr Asp Lys Val Asp Leu Asn Gln
1               5                   10                  15

<210> SEQ ID NO 66
<211> LENGTH: 15
<212> TYPE: PRT
<213> ORGANISM: Helicobacter pylori

<400> SEQUENCE: 66

Ile Thr Asp Lys Val Asp Asn Leu Asn Gln Ala Val Ser Ile Ala

<210> SEQ ID NO 67
<211> LENGTH: 15
<212> TYPE: PRT
<213> ORGANISM: Helicobacter pylori

<400> SEQUENCE: 67

Ile Thr Asp Lys Val Asp Asn Leu Asn Gln Ala Val Ser Glu Ala
1               5                   10                  15

<210> SEQ ID NO 68
<211> LENGTH: 15
<212> TYPE: PRT
<213> ORGANISM: Helicobacter pylori

<400> SEQUENCE: 68

Thr Leu Ala Lys Asn Phe Ser Asp Ile Lys Lys Glu Leu Asn Glu
1               5                   10                  15

<210> SEQ ID NO 69
<211> LENGTH: 15
<212> TYPE: PRT
<213> ORGANISM: Helicobacter pylori

<400> SEQUENCE: 69

Thr Leu Ser Lys Asn Phe Ser Asp Ile Lys Lys Glu Leu Asn Glu
1               5                   10                  15

<210> SEQ ID NO 70
<211> LENGTH: 15
<212> TYPE: PRT
<213> ORGANISM: Helicobacter pylori

<400> SEQUENCE: 70

Asn Leu Ala Lys Asn Phe Ser Asp Ile Lys Lys Glu Leu Asn Glu
1               5                   10                  15

<210> SEQ ID NO 71
<211> LENGTH: 15
<212> TYPE: PRT
<213> ORGANISM: Helicobacter pylori

<400> SEQUENCE: 71

Asn Phe Ser Asp Ile Lys Lys Glu Leu Asn Glu Lys Phe Lys Asn
1               5                   10                  15

<210> SEQ ID NO 72
<211> LENGTH: 15
<212> TYPE: PRT
<213> ORGANISM: Helicobacter pylori

<400> SEQUENCE: 72

Asn Phe Ser Asp Ile Lys Lys Glu Leu Asn Glu Lys Leu Phe Gly
1               5                   10                  15

<210> SEQ ID NO 73
<211> LENGTH: 15
<212> TYPE: PRT
<213> ORGANISM: Helicobacter pylori

<400> SEQUENCE: 73

Lys Asn Ser Thr Glu Pro Ile Tyr Ala Lys Val Asn Lys Lys Lys
1               5                   10                  15

<210> SEQ ID NO 74
<211> LENGTH: 15
<212> TYPE: PRT
<213> ORGANISM: Helicobacter pylori

<400> SEQUENCE: 74

Gly Leu Lys Asn Glu Pro Ile Tyr Ala Lys Val Asn Lys Lys Lys
1               5                   10                  15

<210> SEQ ID NO 75
<211> LENGTH: 15
<212> TYPE: PRT
<213> ORGANISM: Helicobacter pylori

<400> SEQUENCE: 75

Lys Asn Asn Thr Glu Pro Ile Tyr Ala Gln Val Asn Lys Lys Lys
1               5                   10                  15

<210> SEQ ID NO 76
<211> LENGTH: 15
<212> TYPE: PRT
<213> ORGANISM: Helicobacter pylori

<400> SEQUENCE: 76

Lys Asn Ser Gly Glu Pro Ile Tyr Ala Gln Val Asn Lys Lys Lys
1               5                   10                  15

<210> SEQ ID NO 77
<211> LENGTH: 15
<212> TYPE: PRT
<213> ORGANISM: Helicobacter pylori

<400> SEQUENCE: 77

Lys Gly Pro Glu Glu Pro Ile Tyr Ala Lys Val Asn Lys Lys Lys
1               5                   10                  15

<210> SEQ ID NO 78
<211> LENGTH: 15
<212> TYPE: PRT
<213> ORGANISM: Helicobacter pylori

<400> SEQUENCE: 78

Lys Asn Ser Ala Glu Pro Ile Tyr Ala Gln Val Asn Lys Lys Lys
1               5                   10                  15

<210> SEQ ID NO 79
<211> LENGTH: 15
<212> TYPE: PRT
<213> ORGANISM: Helicobacter pylori

<400> SEQUENCE: 79

Lys Asn Ser Gly Glu Pro Ile Tyr Ala Lys Val Asn Lys Lys Lys
1               5                   10                  15

<210> SEQ ID NO 80
<211> LENGTH: 15
<212> TYPE: PRT
<213> ORGANISM: Helicobacter pylori

<400> SEQUENCE: 80

Lys Asn Ser Ala Glu Pro Ile Tyr Ala Lys Val Asn Lys Lys Lys
1               5                   10                  15

<210> SEQ ID NO 81

```
<211> LENGTH: 15
<212> TYPE: PRT
<213> ORGANISM: Helicobacter pylori

<400> SEQUENCE: 81

Glu Asn Ser Thr Glu Pro Ile Tyr Ala Lys Val Asn Lys Lys Lys
1               5                   10                  15

<210> SEQ ID NO 82
<211> LENGTH: 15
<212> TYPE: PRT
<213> ORGANISM: Helicobacter pylori

<400> SEQUENCE: 82

Lys Asn Asn Glu Glu Pro Ile Tyr Ala Gln Val Asn Lys Lys Lys
1               5                   10                  15

<210> SEQ ID NO 83
<211> LENGTH: 15
<212> TYPE: PRT
<213> ORGANISM: Helicobacter pylori

<400> SEQUENCE: 83

Lys Asn Asn Thr Glu Pro Ile Tyr Ala Lys Val Asn Lys Lys Lys
1               5                   10                  15

<210> SEQ ID NO 84
<211> LENGTH: 15
<212> TYPE: PRT
<213> ORGANISM: Helicobacter pylori

<400> SEQUENCE: 84

Glu Pro Ile Tyr Ala Lys Val Asn Lys Lys Lys Thr Gly Gln Val
1               5                   10                  15

<210> SEQ ID NO 85
<211> LENGTH: 15
<212> TYPE: PRT
<213> ORGANISM: Helicobacter pylori

<400> SEQUENCE: 85

Glu Pro Ile Tyr Ala Gln Val Asn Lys Lys Lys Thr Gly Gln Val
1               5                   10                  15

<210> SEQ ID NO 86
<211> LENGTH: 15
<212> TYPE: PRT
<213> ORGANISM: Helicobacter pylori

<400> SEQUENCE: 86

Glu Pro Ile Tyr Ala Lys Val Asn Lys Lys Lys Ala Gly Gln Ala
1               5                   10                  15

<210> SEQ ID NO 87
<211> LENGTH: 15
<212> TYPE: PRT
<213> ORGANISM: Helicobacter pylori

<400> SEQUENCE: 87

Glu Pro Ile Tyr Ala Lys Val Asn Lys Lys Lys Thr Gly Gln Ala
1               5                   10                  15

<210> SEQ ID NO 88
<211> LENGTH: 15
<212> TYPE: PRT
```

-continued

<213> ORGANISM: Helicobacter pylori

<400> SEQUENCE: 88

Glu Pro Ile Tyr Ala Lys Val Asn Lys Lys Ala Gly Gln Val
1               5                   10                  15

<210> SEQ ID NO 89
<211> LENGTH: 15
<212> TYPE: PRT
<213> ORGANISM: Helicobacter pylori

<400> SEQUENCE: 89

Glu Pro Ile Tyr Ala Gln Val Asn Lys Lys Thr Gly Gln Ala
1               5                   10                  15

<210> SEQ ID NO 90
<211> LENGTH: 15
<212> TYPE: PRT
<213> ORGANISM: Helicobacter pylori

<400> SEQUENCE: 90

Glu Pro Ile Tyr Ala Gln Val Asn Lys Lys Ala Gly Gln Ala
1               5                   10                  15

<210> SEQ ID NO 91
<211> LENGTH: 15
<212> TYPE: PRT
<213> ORGANISM: Helicobacter pylori

<400> SEQUENCE: 91

Glu Pro Ile Tyr Ala Gln Val Asn Lys Lys Ala Gly Gln Val
1               5                   10                  15

<210> SEQ ID NO 92
<211> LENGTH: 15
<212> TYPE: PRT
<213> ORGANISM: Helicobacter pylori

<400> SEQUENCE: 92

Glu Pro Ile Tyr Ala Lys Val Asn Lys Lys Thr Gly Glu Val
1               5                   10                  15

<210> SEQ ID NO 93
<211> LENGTH: 15
<212> TYPE: PRT
<213> ORGANISM: Helicobacter pylori

<400> SEQUENCE: 93

Glu Pro Ile Tyr Ala Lys Val Asn Lys Lys Thr Glu Gln Ala
1               5                   10                  15

<210> SEQ ID NO 94
<211> LENGTH: 15
<212> TYPE: PRT
<213> ORGANISM: Helicobacter pylori

<400> SEQUENCE: 94

Val Ala Ser Pro Glu Pro Ile Tyr Ala Gln Val Ala Lys Lys
1               5                   10                  15

<210> SEQ ID NO 95
<211> LENGTH: 15
<212> TYPE: PRT
<213> ORGANISM: Helicobacter pylori

```
<400> SEQUENCE: 95

Val Ala Ser Pro Glu Glu Pro Ile Tyr Thr Gln Val Ala Lys Lys
1               5                   10                  15

<210> SEQ ID NO 96
<211> LENGTH: 15
<212> TYPE: PRT
<213> ORGANISM: Helicobacter pylori

<400> SEQUENCE: 96

Ala Ala Ser Pro Glu Glu Pro Ile Tyr Ala Gln Val Ala Lys Lys
1               5                   10                  15

<210> SEQ ID NO 97
<211> LENGTH: 15
<212> TYPE: PRT
<213> ORGANISM: Helicobacter pylori

<400> SEQUENCE: 97

Ala Thr Ser Pro Glu Glu Pro Ile Tyr Ala Gln Val Ala Lys Lys
1               5                   10                  15

<210> SEQ ID NO 98
<211> LENGTH: 15
<212> TYPE: PRT
<213> ORGANISM: Helicobacter pylori

<400> SEQUENCE: 98

Ala Ala Ser Leu Glu Glu Pro Ile Tyr Ala Gln Val Ala Lys Lys
1               5                   10                  15

<210> SEQ ID NO 99
<211> LENGTH: 15
<212> TYPE: PRT
<213> ORGANISM: Helicobacter pylori

<400> SEQUENCE: 99

Ala Ala Ser Pro Glu Glu Pro Ile Tyr Thr Gln Val Ala Lys Lys
1               5                   10                  15

<210> SEQ ID NO 100
<211> LENGTH: 15
<212> TYPE: PRT
<213> ORGANISM: Helicobacter pylori

<400> SEQUENCE: 100

Ala Ala Ser His Glu Glu Pro Ile Tyr Ala Gln Val Ala Lys Lys
1               5                   10                  15

<210> SEQ ID NO 101
<211> LENGTH: 15
<212> TYPE: PRT
<213> ORGANISM: Helicobacter pylori

<400> SEQUENCE: 101

Val Ala Ser Leu Glu Glu Pro Ile Tyr Thr Gln Val Ala Lys Lys
1               5                   10                  15

<210> SEQ ID NO 102
<211> LENGTH: 15
<212> TYPE: PRT
<213> ORGANISM: Helicobacter pylori

<400> SEQUENCE: 102
```

Leu Glu Asn Ser Thr Glu Pro Ile Tyr Thr Gln Val Ala Lys Lys
1               5                  10                 15

<210> SEQ ID NO 103
<211> LENGTH: 15
<212> TYPE: PRT
<213> ORGANISM: Helicobacter pylori

<400> SEQUENCE: 103

Ala Ser Pro Glu Glu Pro Val Tyr Thr Gln Val Ala Lys Met Val
1               5                  10                 15

<210> SEQ ID NO 104
<211> LENGTH: 15
<212> TYPE: PRT
<213> ORGANISM: Helicobacter pylori

<400> SEQUENCE: 104

Val Ala Ser His Glu Glu Pro Ile Tyr Ala Gln Val Ala Lys Lys
1               5                  10                 15

<210> SEQ ID NO 105
<211> LENGTH: 15
<212> TYPE: PRT
<213> ORGANISM: Helicobacter pylori

<400> SEQUENCE: 105

Glu Glu Pro Ile Tyr Ala Gln Val Ala Lys Lys Val Asn Ala Lys
1               5                  10                 15

<210> SEQ ID NO 106
<211> LENGTH: 15
<212> TYPE: PRT
<213> ORGANISM: Helicobacter pylori

<400> SEQUENCE: 106

Glu Glu Pro Ile Tyr Thr Gln Val Ala Lys Lys Val Asn Ala Lys
1               5                  10                 15

<210> SEQ ID NO 107
<211> LENGTH: 15
<212> TYPE: PRT
<213> ORGANISM: Helicobacter pylori

<400> SEQUENCE: 107

Glu Glu Pro Ile Tyr Ala Gln Val Ala Lys Lys Val Ser Ala Lys
1               5                  10                 15

<210> SEQ ID NO 108
<211> LENGTH: 15
<212> TYPE: PRT
<213> ORGANISM: Helicobacter pylori

<400> SEQUENCE: 108

Glu Glu Pro Ile Tyr Ala Gln Val Ala Lys Lys Val Thr Gln Lys
1               5                  10                 15

<210> SEQ ID NO 109
<211> LENGTH: 15
<212> TYPE: PRT
<213> ORGANISM: Helicobacter pylori

<400> SEQUENCE: 109

Glu Glu Pro Ile Tyr Ala Gln Val Ala Lys Lys Val Thr Lys Lys
1               5                  10                 15

<210> SEQ ID NO 110
<211> LENGTH: 15
<212> TYPE: PRT
<213> ORGANISM: Helicobacter pylori

<400> SEQUENCE: 110

Glu Glu Pro Ile Tyr Thr Gln Val Ala Lys Lys Val Thr Lys Lys
1               5                   10                  15

<210> SEQ ID NO 111
<211> LENGTH: 15
<212> TYPE: PRT
<213> ORGANISM: Helicobacter pylori

<400> SEQUENCE: 111

Glu Glu Pro Ile Tyr Thr Gln Val Ala Lys Lys Val Lys Ala Lys
1               5                   10                  15

<210> SEQ ID NO 112
<211> LENGTH: 15
<212> TYPE: PRT
<213> ORGANISM: Helicobacter pylori

<400> SEQUENCE: 112

Glu Glu Pro Ile Tyr Thr Gln Val Ala Lys Lys Val Thr Gln Lys
1               5                   10                  15

<210> SEQ ID NO 113
<211> LENGTH: 15
<212> TYPE: PRT
<213> ORGANISM: Helicobacter pylori

<400> SEQUENCE: 113

Thr Glu Pro Ile Tyr Thr Gln Val Ala Lys Lys Val Lys Ala Lys
1               5                   10                  15

<210> SEQ ID NO 114
<211> LENGTH: 15
<212> TYPE: PRT
<213> ORGANISM: Helicobacter pylori

<400> SEQUENCE: 114

Glu Glu Pro Val Tyr Thr Gln Val Ala Lys Met Val Thr Gln Lys
1               5                   10                  15

<210> SEQ ID NO 115
<211> LENGTH: 15
<212> TYPE: PRT
<213> ORGANISM: Helicobacter pylori

<400> SEQUENCE: 115

Ala Gln Val Ala Lys Lys Val Asn Ala Lys Ile Asp Arg Leu Asn
1               5                   10                  15

<210> SEQ ID NO 116
<211> LENGTH: 15
<212> TYPE: PRT
<213> ORGANISM: Helicobacter pylori

<400> SEQUENCE: 116

Ala Gln Val Ala Lys Lys Val Ser Ala Lys Ile Asp Gln Leu Asn
1               5                   10                  15

-continued

<210> SEQ ID NO 117
<211> LENGTH: 15
<212> TYPE: PRT
<213> ORGANISM: Helicobacter pylori

<400> SEQUENCE: 117

Thr Gln Val Ala Lys Lys Val Asn Ala Lys Ile Asp Arg Leu Asn
1               5                   10                  15

<210> SEQ ID NO 118
<211> LENGTH: 15
<212> TYPE: PRT
<213> ORGANISM: Helicobacter pylori

<400> SEQUENCE: 118

Ala Gln Val Ala Lys Lys Val Asn Ala Lys Ile Asp Gln Leu Asn
1               5                   10                  15

<210> SEQ ID NO 119
<211> LENGTH: 15
<212> TYPE: PRT
<213> ORGANISM: Helicobacter pylori

<400> SEQUENCE: 119

Thr Gln Val Ala Lys Lys Val Asn Ala Lys Ile Asp Gln Leu Asn
1               5                   10                  15

<210> SEQ ID NO 120
<211> LENGTH: 15
<212> TYPE: PRT
<213> ORGANISM: Helicobacter pylori

<400> SEQUENCE: 120

Thr Gln Val Ala Lys Lys Val Lys Ala Lys Ile Asp Gln Leu Asn
1               5                   10                  15

<210> SEQ ID NO 121
<211> LENGTH: 15
<212> TYPE: PRT
<213> ORGANISM: Helicobacter pylori

<400> SEQUENCE: 121

Thr Gln Val Ala Lys Lys Val Thr Gln Lys Ile Asp Gln Leu Asn
1               5                   10                  15

<210> SEQ ID NO 122
<211> LENGTH: 15
<212> TYPE: PRT
<213> ORGANISM: Helicobacter pylori

<400> SEQUENCE: 122

Lys Lys Val Asn Ala Lys Ile Asp Arg Leu Asn Gln Ile Ala Ser
1               5                   10                  15

<210> SEQ ID NO 123
<211> LENGTH: 15
<212> TYPE: PRT
<213> ORGANISM: Helicobacter pylori

<400> SEQUENCE: 123

Lys Lys Val Asn Ala Lys Ile Asp Gln Leu Asn Gln Ala Ala Ser
1               5                   10                  15

<210> SEQ ID NO 124
<211> LENGTH: 15

<212> TYPE: PRT
<213> ORGANISM: Helicobacter pylori

<400> SEQUENCE: 124

Lys Lys Val Asn Ala Lys Ile Asp Gln Leu Asn Gln Ile Ala Ser
1               5                   10                  15

<210> SEQ ID NO 125
<211> LENGTH: 15
<212> TYPE: PRT
<213> ORGANISM: Helicobacter pylori

<400> SEQUENCE: 125

Lys Lys Val Asn Ala Lys Ile Asp Arg Leu Asn Gln Ala Ala Ser
1               5                   10                  15

<210> SEQ ID NO 126
<211> LENGTH: 15
<212> TYPE: PRT
<213> ORGANISM: Helicobacter pylori

<400> SEQUENCE: 126

Lys Lys Val Lys Ala Lys Ile Asp Gln Leu Asn Gln Ala Ala Ser
1               5                   10                  15

<210> SEQ ID NO 127
<211> LENGTH: 15
<212> TYPE: PRT
<213> ORGANISM: Helicobacter pylori

<400> SEQUENCE: 127

Lys Lys Val Asn Ala Lys Ile Asp Arg Leu Asn Gln Ile Ala Arg
1               5                   10                  15

<210> SEQ ID NO 128
<211> LENGTH: 15
<212> TYPE: PRT
<213> ORGANISM: Helicobacter pylori

<400> SEQUENCE: 128

Lys Lys Val Ser Ala Lys Ile Asp Gln Leu Asn Gln Ala Ala Ser
1               5                   10                  15

<210> SEQ ID NO 129
<211> LENGTH: 15
<212> TYPE: PRT
<213> ORGANISM: Helicobacter pylori

<400> SEQUENCE: 129

Gly Val Gly Gln Ala Ala Gly Phe Pro Leu Lys Arg His Asp Lys
1               5                   10                  15

<210> SEQ ID NO 130
<211> LENGTH: 15
<212> TYPE: PRT
<213> ORGANISM: Helicobacter pylori

<400> SEQUENCE: 130

Gly Val Gly Gln Ala Ala Gly Phe Pro Leu Lys Lys His Asp Lys
1               5                   10                  15

<210> SEQ ID NO 131
<211> LENGTH: 15
<212> TYPE: PRT
<213> ORGANISM: Helicobacter pylori -continued

<400> SEQUENCE: 131

Gly Val Gly Gln Ala Ala Gly Phe Pro Leu Lys Lys His Gly Lys
1               5                   10                  15

<210> SEQ ID NO 132
<211> LENGTH: 15
<212> TYPE: PRT
<213> ORGANISM: Helicobacter pylori

<400> SEQUENCE: 132

Gly Val Gly Gln Ala Ala Ser Phe Pro Leu Lys Arg His Asp Lys
1               5                   10                  15

<210> SEQ ID NO 133
<211> LENGTH: 15
<212> TYPE: PRT
<213> ORGANISM: Helicobacter pylori

<400> SEQUENCE: 133

Gly Val Gly Arg Ala Ala Gly Phe Pro Leu Lys Arg His Asp Lys
1               5                   10                  15

<210> SEQ ID NO 134
<211> LENGTH: 15
<212> TYPE: PRT
<213> ORGANISM: Helicobacter pylori

<400> SEQUENCE: 134

Gly Val Gly Gln Ala Val Gly Phe Pro Leu Lys Arg His Asp Lys
1               5                   10                  15

<210> SEQ ID NO 135
<211> LENGTH: 15
<212> TYPE: PRT
<213> ORGANISM: Helicobacter pylori

<400> SEQUENCE: 135

Gly Val Gly Lys Ala Ala Gly Phe Pro Leu Lys Arg His Asp Lys
1               5                   10                  15

<210> SEQ ID NO 136
<211> LENGTH: 15
<212> TYPE: PRT
<213> ORGANISM: Helicobacter pylori

<400> SEQUENCE: 136

Asp Val Gly Gln Ala Ala Asn Phe Leu Leu Lys Arg His Asp Lys
1               5                   10                  15

<210> SEQ ID NO 137
<211> LENGTH: 15
<212> TYPE: PRT
<213> ORGANISM: Helicobacter pylori

<400> SEQUENCE: 137

Val Val Gly Gln Ala Val Gly Phe Pro Leu Lys Arg His Asp Lys
1               5                   10                  15

<210> SEQ ID NO 138
<211> LENGTH: 15
<212> TYPE: PRT
<213> ORGANISM: Helicobacter pylori

<400> SEQUENCE: 138

Gly Val Gly Gln Ala Gly Tyr Pro Leu Lys Arg His Asp Lys
1               5                   10                  15

<210> SEQ ID NO 139
<211> LENGTH: 15
<212> TYPE: PRT
<213> ORGANISM: Helicobacter pylori

<400> SEQUENCE: 139

Gly Val Gly Gln Ala Thr Gly Phe Pro Leu Lys Arg His Asp Lys
1               5                   10                  15

<210> SEQ ID NO 140
<211> LENGTH: 15
<212> TYPE: PRT
<213> ORGANISM: Helicobacter pylori

<400> SEQUENCE: 140

Gly Val Gly Gln Val Ala Gly Phe Pro Leu Lys Lys His Gly Lys
1               5                   10                  15

<210> SEQ ID NO 141
<211> LENGTH: 15
<212> TYPE: PRT
<213> ORGANISM: Helicobacter pylori

<400> SEQUENCE: 141

Val Gly Gln Ala Gly Phe Pro Leu Lys Arg His Asp Lys Val Asp
1               5                   10                  15

<210> SEQ ID NO 142
<211> LENGTH: 15
<212> TYPE: PRT
<213> ORGANISM: Helicobacter pylori

<400> SEQUENCE: 142

Val Gly Gln Ala Gly Phe Pro Leu Lys Arg His Asp Lys Val Glu
1               5                   10                  15

<210> SEQ ID NO 143
<211> LENGTH: 15
<212> TYPE: PRT
<213> ORGANISM: Helicobacter pylori

<400> SEQUENCE: 143

Val Gly Gln Ala Gly Phe Pro Leu Lys Lys His Ala Lys Val Glu
1               5                   10                  15

<210> SEQ ID NO 144
<211> LENGTH: 15
<212> TYPE: PRT
<213> ORGANISM: Helicobacter pylori

<400> SEQUENCE: 144

Val Asn Gln Ala Gly Phe Pro Leu Lys Arg His Asp Lys Val Asp
1               5                   10                  15

<210> SEQ ID NO 145
<211> LENGTH: 15
<212> TYPE: PRT
<213> ORGANISM: Helicobacter pylori

<400> SEQUENCE: 145

Val Gly Gln Ala Gly Phe Leu Leu Lys Arg His Asp Lys Val Asp

```
1               5                   10                  15
```

<210> SEQ ID NO 146
<211> LENGTH: 15
<212> TYPE: PRT
<213> ORGANISM: Helicobacter pylori

<400> SEQUENCE: 146

```
Ala Gly Phe Pro Leu Lys Arg His Asp Lys Val Asp Asp Leu Ser
1               5                   10                  15
```

<210> SEQ ID NO 147
<211> LENGTH: 15
<212> TYPE: PRT
<213> ORGANISM: Helicobacter pylori

<400> SEQUENCE: 147

```
Gly Pro Phe Pro Leu Lys Arg His Asp Lys Val Asp Asp Leu Ser
1               5                   10                  15
```

<210> SEQ ID NO 148
<211> LENGTH: 15
<212> TYPE: PRT
<213> ORGANISM: Helicobacter pylori

<400> SEQUENCE: 148

```
Ala Gly Phe Pro Leu Lys Arg His Asp Lys Val Glu Asp Leu Ser
1               5                   10                  15
```

<210> SEQ ID NO 149
<211> LENGTH: 15
<212> TYPE: PRT
<213> ORGANISM: Helicobacter pylori

<400> SEQUENCE: 149

```
Ala Gly Phe Pro Leu Lys Lys His Asp Lys Val Asp Asp Leu Ser
1               5                   10                  15
```

<210> SEQ ID NO 150
<211> LENGTH: 15
<212> TYPE: PRT
<213> ORGANISM: Helicobacter pylori

<400> SEQUENCE: 150

```
Ala Gly Phe Pro Leu Lys Lys His Ala Lys Val Glu Asp Leu Ser
1               5                   10                  15
```

<210> SEQ ID NO 151
<211> LENGTH: 15
<212> TYPE: PRT
<213> ORGANISM: Helicobacter pylori

<400> SEQUENCE: 151

```
Ala Gly Phe Pro Leu Lys Lys His Asp Lys Val Glu Asp Leu Ser
1               5                   10                  15
```

<210> SEQ ID NO 152
<211> LENGTH: 15
<212> TYPE: PRT
<213> ORGANISM: Helicobacter pylori

<400> SEQUENCE: 152

```
Ala Ser Phe Pro Leu Lys Arg His Asp Lys Val Asp Asp Leu Ser
1               5                   10                  15
```

<210> SEQ ID NO 153
<211> LENGTH: 15
<212> TYPE: PRT
<213> ORGANISM: Helicobacter pylori

<400> SEQUENCE: 153

Glu Gly Phe Pro Leu Lys Arg His Asp Lys Val Asp Asp Leu Ser
1               5                   10                  15

<210> SEQ ID NO 154
<211> LENGTH: 15
<212> TYPE: PRT
<213> ORGANISM: Helicobacter pylori

<400> SEQUENCE: 154

Ala Gly Phe Pro Leu Lys Lys His Gly Lys Val Asp Asp Leu Ser
1               5                   10                  15

<210> SEQ ID NO 155
<211> LENGTH: 15
<212> TYPE: PRT
<213> ORGANISM: Helicobacter pylori

<400> SEQUENCE: 155

Ala Gly Phe Pro Leu Lys Arg His Asp Lys Val Gly Asp Leu Ser
1               5                   10                  15

<210> SEQ ID NO 156
<211> LENGTH: 15
<212> TYPE: PRT
<213> ORGANISM: Helicobacter pylori

<400> SEQUENCE: 156

Gly Ser Phe Pro Leu Lys Arg His Asp Lys Val Glu Asp Leu Ser
1               5                   10                  15

<210> SEQ ID NO 157
<211> LENGTH: 15
<212> TYPE: PRT
<213> ORGANISM: Helicobacter pylori

<400> SEQUENCE: 157

Ala Gly Tyr Pro Leu Lys Arg His Asp Lys Val Asp Asp Leu Ser
1               5                   10                  15

<210> SEQ ID NO 158
<211> LENGTH: 15
<212> TYPE: PRT
<213> ORGANISM: Helicobacter pylori

<400> SEQUENCE: 158

Gly Ser Ser Pro Leu Lys Arg His Ala Lys Val Asp Asp Leu Ser
1               5                   10                  15

<210> SEQ ID NO 159
<211> LENGTH: 15
<212> TYPE: PRT
<213> ORGANISM: Helicobacter pylori

<400> SEQUENCE: 159

Thr Gly Phe Pro Leu Lys Arg His Asp Lys Val Asp Asp Leu Ser
1               5                   10                  15

<210> SEQ ID NO 160

```
<211> LENGTH: 15
<212> TYPE: PRT
<213> ORGANISM: Helicobacter pylori

<400> SEQUENCE: 160

Gly Pro Phe Pro Leu Lys Lys His Ala Lys Val Asp Asp Leu Ser
1               5                   10                  15

<210> SEQ ID NO 161
<211> LENGTH: 15
<212> TYPE: PRT
<213> ORGANISM: Helicobacter pylori

<400> SEQUENCE: 161

Leu Lys Arg His Asp Lys Val Asp Asp Leu Ser Lys Val Gly Leu
1               5                   10                  15

<210> SEQ ID NO 162
<211> LENGTH: 15
<212> TYPE: PRT
<213> ORGANISM: Helicobacter pylori

<400> SEQUENCE: 162

Leu Lys Arg His Asp Lys Val Asp Asp Leu Ser Lys Val Gly Arg
1               5                   10                  15

<210> SEQ ID NO 163
<211> LENGTH: 15
<212> TYPE: PRT
<213> ORGANISM: Helicobacter pylori

<400> SEQUENCE: 163

Leu Lys Arg His Asp Lys Val Glu Asp Leu Ser Lys Val Gly Arg
1               5                   10                  15

<210> SEQ ID NO 164
<211> LENGTH: 15
<212> TYPE: PRT
<213> ORGANISM: Helicobacter pylori

<400> SEQUENCE: 164

Leu Lys Arg His Asp Lys Val Glu Asp Leu Ser Lys Val Gly Leu
1               5                   10                  15

<210> SEQ ID NO 165
<211> LENGTH: 15
<212> TYPE: PRT
<213> ORGANISM: Helicobacter pylori

<400> SEQUENCE: 165

Leu Lys Arg His Asp Lys Val Gly Asp Leu Ser Lys Val Gly Leu
1               5                   10                  15

<210> SEQ ID NO 166
<211> LENGTH: 15
<212> TYPE: PRT
<213> ORGANISM: Helicobacter pylori

<400> SEQUENCE: 166

Leu Lys Lys His Asp Lys Val Glu Asp Leu Ser Lys Val Gly Arg
1               5                   10                  15

<210> SEQ ID NO 167
<211> LENGTH: 15
<212> TYPE: PRT
```

<213> ORGANISM: Helicobacter pylori

<400> SEQUENCE: 167

Leu Lys Lys His Asp Lys Val Asp Asp Leu Ser Lys Val Gly Arg
1               5                   10                  15

<210> SEQ ID NO 168
<211> LENGTH: 15
<212> TYPE: PRT
<213> ORGANISM: Helicobacter pylori

<400> SEQUENCE: 168

Leu Lys Arg His Ala Lys Val Asp Asp Leu Ser Lys Val Gly Leu
1               5                   10                  15

<210> SEQ ID NO 169
<211> LENGTH: 15
<212> TYPE: PRT
<213> ORGANISM: Helicobacter pylori

<400> SEQUENCE: 169

Leu Lys Lys His Asp Lys Val Asp Asp Leu Ser Lys Val Gly Leu
1               5                   10                  15

<210> SEQ ID NO 170
<211> LENGTH: 15
<212> TYPE: PRT
<213> ORGANISM: Helicobacter pylori

<400> SEQUENCE: 170

Leu Lys Lys His Gly Lys Val Asp Asp Leu Ser Lys Val Gly Leu
1               5                   10                  15

<210> SEQ ID NO 171
<211> LENGTH: 15
<212> TYPE: PRT
<213> ORGANISM: Helicobacter pylori

<400> SEQUENCE: 171

Arg Ser Val Ser Pro Glu Pro Ile Tyr Ala Thr Ile Asp Asp Leu
1               5                   10                  15

<210> SEQ ID NO 172
<211> LENGTH: 15
<212> TYPE: PRT
<213> ORGANISM: Helicobacter pylori

<400> SEQUENCE: 172

Leu Ser Ala Ser Pro Glu Pro Ile Tyr Ala Thr Ile Asp Asp Leu
1               5                   10                  15

<210> SEQ ID NO 173
<211> LENGTH: 15
<212> TYPE: PRT
<213> ORGANISM: Helicobacter pylori

<400> SEQUENCE: 173

Ser Ala Ser Pro Glu Pro Ile Tyr Ala Thr Ile Asp Phe Asp Glu
1               5                   10                  15

<210> SEQ ID NO 174
<211> LENGTH: 15
<212> TYPE: PRT
<213> ORGANISM: Helicobacter pylori

```
<400> SEQUENCE: 174

Leu Ser Ala Asn Pro Glu Pro Ile Tyr Ala Thr Ile Asp Asp Leu
1               5                   10                  15

<210> SEQ ID NO 175
<211> LENGTH: 15
<212> TYPE: PRT
<213> ORGANISM: Helicobacter pylori

<400> SEQUENCE: 175

Arg Leu Asp Ser Pro Glu Pro Ile Tyr Ala Thr Ile Asp Asp Leu
1               5                   10                  15

<210> SEQ ID NO 176
<211> LENGTH: 15
<212> TYPE: PRT
<213> ORGANISM: Helicobacter pylori

<400> SEQUENCE: 176

Leu Ser Ala Asn His Glu Pro Ile Tyr Ala Thr Ile Asp Asp Leu
1               5                   10                  15

<210> SEQ ID NO 177
<211> LENGTH: 15
<212> TYPE: PRT
<213> ORGANISM: Helicobacter pylori

<400> SEQUENCE: 177

Asn Ser Asp Arg Ser Glu Pro Ile Tyr Ala Thr Ile Asp Asp Leu
1               5                   10                  15

<210> SEQ ID NO 178
<211> LENGTH: 15
<212> TYPE: PRT
<213> ORGANISM: Helicobacter pylori

<400> SEQUENCE: 178

Leu Ser Ala Ser Pro Glu Pro Ile Tyr Ala Thr Ile Asp Glu Leu
1               5                   10                  15

<210> SEQ ID NO 179
<211> LENGTH: 15
<212> TYPE: PRT
<213> ORGANISM: Helicobacter pylori

<400> SEQUENCE: 179

Pro Glu Pro Ile Tyr Ala Thr Ile Asp Asp Leu Gly Gly Pro Phe
1               5                   10                  15

<210> SEQ ID NO 180
<211> LENGTH: 15
<212> TYPE: PRT
<213> ORGANISM: Helicobacter pylori

<400> SEQUENCE: 180

Pro Glu Pro Ile Tyr Ala Thr Ile Asp Asp Leu Gly Gly Ser Phe
1               5                   10                  15

<210> SEQ ID NO 181
<211> LENGTH: 15
<212> TYPE: PRT
<213> ORGANISM: Helicobacter pylori

<400> SEQUENCE: 181
```

Pro Glu Pro Ile Tyr Ala Thr Ile Asp Glu Leu Gly Gly Pro Phe
1               5                   10                  15

<210> SEQ ID NO 182
<211> LENGTH: 15
<212> TYPE: PRT
<213> ORGANISM: Helicobacter pylori

<400> SEQUENCE: 182

Ser Glu Pro Ile Tyr Ala Thr Ile Asp Asp Leu Gly Gly Pro Phe
1               5                   10                  15

<210> SEQ ID NO 183
<211> LENGTH: 15
<212> TYPE: PRT
<213> ORGANISM: Helicobacter pylori

<400> SEQUENCE: 183

His Glu Pro Ile Tyr Ala Thr Ile Asp Asp Leu Asp Gly Pro Phe
1               5                   10                  15

<210> SEQ ID NO 184
<211> LENGTH: 15
<212> TYPE: PRT
<213> ORGANISM: Helicobacter pylori

<400> SEQUENCE: 184

His Glu Pro Ile Tyr Ala Thr Ile Asp Asp Leu Gly Gly Pro Phe
1               5                   10                  15

<210> SEQ ID NO 185
<211> LENGTH: 15
<212> TYPE: PRT
<213> ORGANISM: Helicobacter pylori

<400> SEQUENCE: 185

Glu Pro Ile Tyr Ala Thr Ile Asp Asp Leu Asp Gly Ser Ser Pro
1               5                   10                  15

<210> SEQ ID NO 186
<211> LENGTH: 15
<212> TYPE: PRT
<213> ORGANISM: Helicobacter pylori

<400> SEQUENCE: 186

Ile Asp Asp Leu Gly Gly Pro Phe Pro Leu Lys Arg His Asp Lys
1               5                   10                  15

<210> SEQ ID NO 187
<211> LENGTH: 15
<212> TYPE: PRT
<213> ORGANISM: Helicobacter pylori

<400> SEQUENCE: 187

Arg His Asp Lys Val Asp Asp Leu Ser Lys Val Gly Arg Ser Val
1               5                   10                  15

<210> SEQ ID NO 188
<211> LENGTH: 15
<212> TYPE: PRT
<213> ORGANISM: Helicobacter pylori

<400> SEQUENCE: 188

Asp Leu Asn Gln Ala Val Ser Glu Ala Lys Ile Gly His Phe Asp
1               5                   10                  15

<210> SEQ ID NO 189
<211> LENGTH: 15
<212> TYPE: PRT
<213> ORGANISM: Helicobacter pylori

<400> SEQUENCE: 189

Asn Gly Ala Ile Asn Glu Lys Ala Thr Gly Met Leu Thr Gln Lys
1               5                   10                  15

<210> SEQ ID NO 190
<211> LENGTH: 15
<212> TYPE: PRT
<213> ORGANISM: Helicobacter pylori

<400> SEQUENCE: 190

Asn Gly Thr Ile Asn Glu Lys Ala Thr Gly Met Leu Thr Gln Lys
1               5                   10                  15

<210> SEQ ID NO 191
<211> LENGTH: 15
<212> TYPE: PRT
<213> ORGANISM: Helicobacter pylori

<400> SEQUENCE: 191

Ser Gly Thr Ile Asn Glu Lys Ala Thr Gly Met Leu Thr Gln Lys
1               5                   10                  15

<210> SEQ ID NO 192
<211> LENGTH: 15
<212> TYPE: PRT
<213> ORGANISM: Helicobacter pylori

<400> SEQUENCE: 192

Thr Gly Thr Ile Asn Glu Lys Ala Thr Gly Met Leu Thr Gln Lys
1               5                   10                  15

<210> SEQ ID NO 193
<211> LENGTH: 15
<212> TYPE: PRT
<213> ORGANISM: Helicobacter pylori

<400> SEQUENCE: 193

Glu Lys Ala Thr Gly Met Leu Thr Gln Lys Asn Pro Glu Trp Leu
1               5                   10                  15

<210> SEQ ID NO 194
<211> LENGTH: 15
<212> TYPE: PRT
<213> ORGANISM: Helicobacter pylori

<400> SEQUENCE: 194

Glu Lys Val Thr Gly Met Leu Thr Gln Lys Asn Pro Glu Trp Leu
1               5                   10                  15

<210> SEQ ID NO 195
<211> LENGTH: 15
<212> TYPE: PRT
<213> ORGANISM: Helicobacter pylori

<400> SEQUENCE: 195

Leu Ser Glu Tyr Asp Lys Ile Gly Phe Asn Gln Lys Asn Met Lys
1               5                   10                  15

-continued

<210> SEQ ID NO 196
<211> LENGTH: 15
<212> TYPE: PRT
<213> ORGANISM: Helicobacter pylori

<400> SEQUENCE: 196

Leu Ser Ala Tyr Asp Lys Ile Gly Phe Asn Gln Lys Asn Met Lys
1               5                   10                  15

<210> SEQ ID NO 197
<211> LENGTH: 15
<212> TYPE: PRT
<213> ORGANISM: Helicobacter pylori

<400> SEQUENCE: 197

Leu Ser Asp Tyr Asp Lys Ile Gly Phe Asn Gln Lys Asn Met Lys
1               5                   10                  15

<210> SEQ ID NO 198
<211> LENGTH: 15
<212> TYPE: PRT
<213> ORGANISM: Helicobacter pylori

<400> SEQUENCE: 198

Leu Ser Glu Tyr Asp Asn Ile Gly Phe Asn Gln Lys Asn Met Lys
1               5                   10                  15

<210> SEQ ID NO 199
<211> LENGTH: 15
<212> TYPE: PRT
<213> ORGANISM: Helicobacter pylori

<400> SEQUENCE: 199

Leu Leu Glu Tyr Asp Lys Ile Gly Phe Asn Gln Lys Asn Met Lys
1               5                   10                  15

<210> SEQ ID NO 200
<211> LENGTH: 15
<212> TYPE: PRT
<213> ORGANISM: Helicobacter pylori

<400> SEQUENCE: 200

Leu Ser Glu Tyr Asp Lys Ile Gly Phe Ser Gln Lys Asn Met Lys
1               5                   10                  15

<210> SEQ ID NO 201
<211> LENGTH: 15
<212> TYPE: PRT
<213> ORGANISM: Helicobacter pylori

<400> SEQUENCE: 201

Leu Ser Glu Tyr Asp Lys Ile Gly Phe Asn Gln Lys Ser Met Lys
1               5                   10                  15

<210> SEQ ID NO 202
<211> LENGTH: 15
<212> TYPE: PRT
<213> ORGANISM: Helicobacter pylori

<400> SEQUENCE: 202

Leu Ser Asp Tyr Asp Lys Ile Gly Phe Asn Gln Lys Asp Met Lys
1               5                   10                  15

<210> SEQ ID NO 203
<211> LENGTH: 15

<212> TYPE: PRT
<213> ORGANISM: Helicobacter pylori

<400> SEQUENCE: 203

Lys Asp Tyr Ser Asp Ser Phe Lys Phe Ser Thr Lys Leu Asn Asn
1               5                   10                  15

<210> SEQ ID NO 204
<211> LENGTH: 15
<212> TYPE: PRT
<213> ORGANISM: Helicobacter pylori

<400> SEQUENCE: 204

Lys Asp Tyr Ser Asp Ser Phe Lys Phe Ser Thr Lys Leu Ser Asn
1               5                   10                  15

<210> SEQ ID NO 205
<211> LENGTH: 15
<212> TYPE: PRT
<213> ORGANISM: Helicobacter pylori

<400> SEQUENCE: 205

Lys Asp Tyr Ser Asp Ser Phe Lys Phe Ser Thr Lys Leu Asn Asp
1               5                   10                  15

<210> SEQ ID NO 206
<211> LENGTH: 15
<212> TYPE: PRT
<213> ORGANISM: Helicobacter pylori

<400> SEQUENCE: 206

Lys Asp Tyr Ser Asp Ser Phe Lys Phe Ser Thr Arg Leu Asn Asn
1               5                   10                  15

<210> SEQ ID NO 207
<211> LENGTH: 15
<212> TYPE: PRT
<213> ORGANISM: Helicobacter pylori

<400> SEQUENCE: 207

Lys Asp Tyr Ser Asp Ser Phe Lys Phe Ser Ile Lys Leu Ser Asn
1               5                   10                  15

<210> SEQ ID NO 208
<211> LENGTH: 15
<212> TYPE: PRT
<213> ORGANISM: Helicobacter pylori

<400> SEQUENCE: 208

Asn Lys Ser Asn Asp Leu Ile Asn Lys Asp Ala Leu Ile Asp Val
1               5                   10                  15

<210> SEQ ID NO 209
<211> LENGTH: 15
<212> TYPE: PRT
<213> ORGANISM: Helicobacter pylori

<400> SEQUENCE: 209

Thr Thr Thr Asp Ile Gln Gly Leu Pro Pro Glu Ser Arg Asp Leu
1               5                   10                  15

<210> SEQ ID NO 210
<211> LENGTH: 15
<212> TYPE: PRT
<213> ORGANISM: Helicobacter pylori

<400> SEQUENCE: 210

Ser Thr Thr His Ile Gln Gly Leu Pro Pro Glu Ser Arg Asp Leu
1               5                   10                  15

<210> SEQ ID NO 211
<211> LENGTH: 15
<212> TYPE: PRT
<213> ORGANISM: Helicobacter pylori

<400> SEQUENCE: 211

Ser Phe Ile Phe Asp Lys Lys Gln Ser Ser Asp Val Lys Glu Ala
1               5                   10                  15

<210> SEQ ID NO 212
<211> LENGTH: 15
<212> TYPE: PRT
<213> ORGANISM: Helicobacter pylori

<400> SEQUENCE: 212

Ser Phe Val Phe Asp Lys Lys Gln Ser Ser Asp Leu Lys Glu Thr
1               5                   10                  15

<210> SEQ ID NO 213
<211> LENGTH: 15
<212> TYPE: PRT
<213> ORGANISM: Helicobacter pylori

<400> SEQUENCE: 213

Ser Phe Ala Phe Asp Lys Lys Gln Ser Ser Asp Leu Lys Glu Thr
1               5                   10                  15

<210> SEQ ID NO 214
<211> LENGTH: 15
<212> TYPE: PRT
<213> ORGANISM: Helicobacter pylori

<400> SEQUENCE: 214

Glu Ser Arg Asp Leu Leu Asp Glu Arg Gly Asn Phe Phe Lys Phe
1               5                   10                  15

<210> SEQ ID NO 215
<211> LENGTH: 15
<212> TYPE: PRT
<213> ORGANISM: Helicobacter pylori

<400> SEQUENCE: 215

Glu Ala Arg Asp Leu Leu Asp Glu Arg Gly Asp Phe Ser Lys Phe
1               5                   10                  15

<210> SEQ ID NO 216
<211> LENGTH: 15
<212> TYPE: PRT
<213> ORGANISM: Helicobacter pylori

<400> SEQUENCE: 216

Glu Ala Arg Asp Leu Leu Asp Glu Arg Gly Asn Phe Phe Lys Phe
1               5                   10                  15

<210> SEQ ID NO 217
<211> LENGTH: 15
<212> TYPE: PRT
<213> ORGANISM: Helicobacter pylori

<400> SEQUENCE: 217

Leu Thr Pro Glu Ala Arg Lys Leu Leu Glu Glu Ala Lys Lys Ser
1               5                   10                  15

<210> SEQ ID NO 218
<211> LENGTH: 15
<212> TYPE: PRT
<213> ORGANISM: Helicobacter pylori

<400> SEQUENCE: 218

Asn Ser Gln Lys Asp Glu Ile Phe Ala Leu Ile Ser Lys Glu Ala
1               5                   10                  15

<210> SEQ ID NO 219
<211> LENGTH: 15
<212> TYPE: PRT
<213> ORGANISM: Helicobacter pylori

<400> SEQUENCE: 219

Asn Ser Gln Lys Asp Glu Ile Phe Ala Leu Ile Asn Gln Glu Thr
1               5                   10                  15

<210> SEQ ID NO 220
<211> LENGTH: 15
<212> TYPE: PRT
<213> ORGANISM: Helicobacter pylori

<400> SEQUENCE: 220

Asn Ser Gln Lys Asn Glu Ile Phe Ala Leu Ile Asn Lys Glu Ala
1               5                   10                  15

<210> SEQ ID NO 221
<211> LENGTH: 15
<212> TYPE: PRT
<213> ORGANISM: Helicobacter pylori

<400> SEQUENCE: 221

Asn Ser Gln Lys Asp Glu Ile Phe Lys Leu Ile Asn Glu Gly Ala
1               5                   10                  15

<210> SEQ ID NO 222
<211> LENGTH: 15
<212> TYPE: PRT
<213> ORGANISM: Helicobacter pylori

<400> SEQUENCE: 222

Asn Ser Gln Lys Asp Glu Ile Leu Ala Leu Ile Asn Lys Glu Ala
1               5                   10                  15

<210> SEQ ID NO 223
<211> LENGTH: 15
<212> TYPE: PRT
<213> ORGANISM: Helicobacter pylori

<400> SEQUENCE: 223

Val Asn Lys Asp Leu Lys Asp Phe Ser Lys Ser Phe Asp Glu Phe
1               5                   10                  15

<210> SEQ ID NO 224
<211> LENGTH: 15
<212> TYPE: PRT
<213> ORGANISM: Helicobacter pylori

<400> SEQUENCE: 224

Ile Asn Lys Asp Leu Lys Asp Phe Ser Lys Ser Phe Asp Asp Phe

<210> SEQ ID NO 225
<211> LENGTH: 15
<212> TYPE: PRT
<213> ORGANISM: Helicobacter pylori

<400> SEQUENCE: 225

Ile Asn Lys Asn Leu Lys Asp Phe Ser Lys Ser Phe Asp Glu Phe
1               5                   10                  15

<210> SEQ ID NO 226
<211> LENGTH: 15
<212> TYPE: PRT
<213> ORGANISM: Helicobacter pylori

<400> SEQUENCE: 226

Ile Ser Lys Asp Leu Lys Asp Phe Ser Lys Ser Phe Asp Glu Phe
1               5                   10                  15

<210> SEQ ID NO 227
<211> LENGTH: 15
<212> TYPE: PRT
<213> ORGANISM: Helicobacter pylori

<400> SEQUENCE: 227

Lys Ser Phe Asp Gly Phe Lys Asn Gly Lys Asn Lys Asp Phe Ser
1               5                   10                  15

<210> SEQ ID NO 228
<211> LENGTH: 15
<212> TYPE: PRT
<213> ORGANISM: Helicobacter pylori

<400> SEQUENCE: 228

Lys Ile Glu Asn Leu Asn Val Ala Leu Asn Asp Phe Lys Asn Gly
1               5                   10                  15

<210> SEQ ID NO 229
<211> LENGTH: 15
<212> TYPE: PRT
<213> ORGANISM: Helicobacter pylori

<400> SEQUENCE: 229

Glu Trp Ile Ser Lys Ile Glu Asn Leu Asn Val Ala Leu Asn Asp
1               5                   10                  15

<210> SEQ ID NO 230
<211> LENGTH: 15
<212> TYPE: PRT
<213> ORGANISM: Helicobacter pylori

<400> SEQUENCE: 230

Glu Trp Val Ser Lys Val Glu Asn Leu Asn Ala Ala Leu Asn Glu
1               5                   10                  15

<210> SEQ ID NO 231
<211> LENGTH: 15
<212> TYPE: PRT
<213> ORGANISM: Helicobacter pylori

<400> SEQUENCE: 231

Glu Trp Ile Ser Lys Val Glu Asn Leu Asn Ala Ala Leu Asn Asp
1               5                   10                  15

```
<210> SEQ ID NO 232
<211> LENGTH: 15
<212> TYPE: PRT
<213> ORGANISM: Helicobacter pylori

<400> SEQUENCE: 232

Lys Val Glu Asn Leu Asn Ala Ala Leu Asn Glu Phe Lys Asn Ser
1               5                   10                  15

<210> SEQ ID NO 233
<211> LENGTH: 15
<212> TYPE: PRT
<213> ORGANISM: Helicobacter pylori

<400> SEQUENCE: 233

Lys Val Glu Asn Leu Asn Ala Ala Leu Asn Glu Phe Lys Ser Gly
1               5                   10                  15

<210> SEQ ID NO 234
<211> LENGTH: 15
<212> TYPE: PRT
<213> ORGANISM: Helicobacter pylori

<400> SEQUENCE: 234

Glu Trp Ile Ser Lys Ile Glu Asn Leu Asn Ala Ala Leu Asn Asp
1               5                   10                  15

<210> SEQ ID NO 235
<211> LENGTH: 15
<212> TYPE: PRT
<213> ORGANISM: Helicobacter pylori

<400> SEQUENCE: 235

Ile Ile Asn Gln Lys Ile Thr Asp Lys Val Gly Asn Leu Ser Ser
1               5                   10                  15

<210> SEQ ID NO 236
<211> LENGTH: 15
<212> TYPE: PRT
<213> ORGANISM: Helicobacter pylori

<400> SEQUENCE: 236

Ile Thr Asp Lys Val Asp Asn Leu Asn Gln Ala Val Leu Val Ala
1               5                   10                  15

<210> SEQ ID NO 237
<211> LENGTH: 15
<212> TYPE: PRT
<213> ORGANISM: Helicobacter pylori

<400> SEQUENCE: 237

Lys Val Asp Asn Leu Asn Gln Ala Val Ser Glu Ala Lys Ala Thr
1               5                   10                  15

<210> SEQ ID NO 238
<211> LENGTH: 15
<212> TYPE: PRT
<213> ORGANISM: Helicobacter pylori

<400> SEQUENCE: 238

Lys Val Asp Asn Leu Asn Gln Ala Val Ser Glu Ala Lys Leu Thr
1               5                   10                  15

<210> SEQ ID NO 239
```

```
<211> LENGTH: 15
<212> TYPE: PRT
<213> ORGANISM: Helicobacter pylori

<400> SEQUENCE: 239

Val Thr Asp Lys Val Asp Asn Leu Asn Gln Ala Val Ser Ile Ala
1               5                   10                  15

<210> SEQ ID NO 240
<211> LENGTH: 15
<212> TYPE: PRT
<213> ORGANISM: Helicobacter pylori

<400> SEQUENCE: 240

Ile Thr Asp Lys Val Asp Asn Leu Asn Gln Ala Val Ser Met Ala
1               5                   10                  15

<210> SEQ ID NO 241
<211> LENGTH: 15
<212> TYPE: PRT
<213> ORGANISM: Helicobacter pylori

<400> SEQUENCE: 241

Val Thr Asp Lys Val Asp Asn Leu Asn Gln Glu Val Ser Val Ala
1               5                   10                  15

<210> SEQ ID NO 242
<211> LENGTH: 15
<212> TYPE: PRT
<213> ORGANISM: Helicobacter pylori

<400> SEQUENCE: 242

Val Thr Asp Lys Val Asp Asn Leu Asn Gln Ala Val Ser Met Ala
1               5                   10                  15

<210> SEQ ID NO 243
<211> LENGTH: 15
<212> TYPE: PRT
<213> ORGANISM: Helicobacter pylori

<400> SEQUENCE: 243

Ile Thr Asp Lys Val Asp Asn Leu Asn Gln Ala Val Ser Glu Thr
1               5                   10                  15

<210> SEQ ID NO 244
<211> LENGTH: 15
<212> TYPE: PRT
<213> ORGANISM: Helicobacter pylori

<400> SEQUENCE: 244

Val Thr Asp Lys Val Asp Asn Leu Asn Gln Ala Val Ser Val Ala
1               5                   10                  15

<210> SEQ ID NO 245
<211> LENGTH: 15
<212> TYPE: PRT
<213> ORGANISM: Helicobacter pylori

<400> SEQUENCE: 245

Ile Thr Asp Lys Val Asp Asn Leu Asn Gln Ala Val Ser Val Ala
1               5                   10                  15

<210> SEQ ID NO 246
<211> LENGTH: 15
<212> TYPE: PRT
```

<213> ORGANISM: Helicobacter pylori

<400> SEQUENCE: 246

Lys Val Asp Asn Leu Asn Gln Ala Val Ser Ile Ala Lys Glu Thr
1               5                   10                  15

<210> SEQ ID NO 247
<211> LENGTH: 15
<212> TYPE: PRT
<213> ORGANISM: Helicobacter pylori

<400> SEQUENCE: 247

Lys Val Asp Asn Leu Asn Gln Ala Val Ser Val Ala Lys Ile Thr
1               5                   10                  15

<210> SEQ ID NO 248
<211> LENGTH: 15
<212> TYPE: PRT
<213> ORGANISM: Helicobacter pylori

<400> SEQUENCE: 248

Ile Thr Asp Lys Val Asp Asp Leu Asn Gln Ala Val Ser Val Ala
1               5                   10                  15

<210> SEQ ID NO 249
<211> LENGTH: 15
<212> TYPE: PRT
<213> ORGANISM: Helicobacter pylori

<400> SEQUENCE: 249

Lys Val Asp Asn Leu Asn Gln Ala Val Ser Ile Ala Lys Ala Thr
1               5                   10                  15

<210> SEQ ID NO 250
<211> LENGTH: 15
<212> TYPE: PRT
<213> ORGANISM: Helicobacter pylori

<400> SEQUENCE: 250

Lys Val Asp Asn Leu Ser Gln Ala Val Ser Val Ala Lys Ile Ala
1               5                   10                  15

<210> SEQ ID NO 251
<211> LENGTH: 15
<212> TYPE: PRT
<213> ORGANISM: Helicobacter pylori

<400> SEQUENCE: 251

Lys Val Asp Asp Leu Asn Gln Ala Val Ser Val Ala Lys Ala Thr
1               5                   10                  15

<210> SEQ ID NO 252
<211> LENGTH: 15
<212> TYPE: PRT
<213> ORGANISM: Helicobacter pylori

<400> SEQUENCE: 252

Ile Thr Asp Lys Val Asp Asp Leu Asn Gln Ala Val Leu Val Ala
1               5                   10                  15

<210> SEQ ID NO 253
<211> LENGTH: 15
<212> TYPE: PRT
<213> ORGANISM: Helicobacter pylori

<400> SEQUENCE: 253

Ile Thr Asn Lys Val Asp Asp Leu Asn Gln Ala Val Ser Val Ala
1               5                   10                  15

<210> SEQ ID NO 254
<211> LENGTH: 15
<212> TYPE: PRT
<213> ORGANISM: Helicobacter pylori

<400> SEQUENCE: 254

Lys Val Asp Asn Leu Ser Ser Ala Val Ser Val Ala Lys Ala Met
1               5                   10                  15

<210> SEQ ID NO 255
<211> LENGTH: 15
<212> TYPE: PRT
<213> ORGANISM: Helicobacter pylori

<400> SEQUENCE: 255

Val Thr Asp Lys Val Asp Asp Leu Asn Gln Ala Val Ser Val Ala
1               5                   10                  15

<210> SEQ ID NO 256
<211> LENGTH: 15
<212> TYPE: PRT
<213> ORGANISM: Helicobacter pylori

<400> SEQUENCE: 256

Ile Thr Asp Lys Val Asp Asp Leu Asn Gln Ala Val Ser Met Ala
1               5                   10                  15

<210> SEQ ID NO 257
<211> LENGTH: 15
<212> TYPE: PRT
<213> ORGANISM: Helicobacter pylori

<400> SEQUENCE: 257

Thr Leu Ser Lys Asn Phe Ser Asp Ile Lys Lys Glu Leu Asn Ala
1               5                   10                  15

<210> SEQ ID NO 258
<211> LENGTH: 15
<212> TYPE: PRT
<213> ORGANISM: Helicobacter pylori

<400> SEQUENCE: 258

Thr Leu Thr Lys Lys Phe Ser Asp Ile Lys Lys Glu Leu Asn Glu
1               5                   10                  15

<210> SEQ ID NO 259
<211> LENGTH: 15
<212> TYPE: PRT
<213> ORGANISM: Helicobacter pylori

<400> SEQUENCE: 259

Asn Leu Thr Lys Asn Phe Ser Asp Ile Arg Lys Glu Leu Asn Glu
1               5                   10                  15

<210> SEQ ID NO 260
<211> LENGTH: 15
<212> TYPE: PRT
<213> ORGANISM: Helicobacter pylori

<400> SEQUENCE: 260

```
Thr Leu Thr Lys Asn Phe Ser Asp Ile Arg Lys Glu Leu Asn Glu
1               5                   10                  15

<210> SEQ ID NO 261
<211> LENGTH: 15
<212> TYPE: PRT
<213> ORGANISM: Helicobacter pylori

<400> SEQUENCE: 261

Asn Glu Lys Phe Lys Asn Phe Asn Asn Asn Asn Gly Leu Lys
1               5                   10                  15

<210> SEQ ID NO 262
<211> LENGTH: 15
<212> TYPE: PRT
<213> ORGANISM: Helicobacter pylori

<400> SEQUENCE: 262

Asn Ser Asn Gly Leu Lys Asn Ser Ala Glu Pro Ile Tyr Ala Gln
1               5                   10                  15

<210> SEQ ID NO 263
<211> LENGTH: 15
<212> TYPE: PRT
<213> ORGANISM: Helicobacter pylori

<400> SEQUENCE: 263

Asn Asn Asn Gly Leu Lys Asn Ser Thr Glu Pro Ile Tyr Ala Lys
1               5                   10                  15

<210> SEQ ID NO 264
<211> LENGTH: 15
<212> TYPE: PRT
<213> ORGANISM: Helicobacter pylori

<400> SEQUENCE: 264

Thr Gln Val Ala Lys Lys Val Lys Ala Lys Ile Asp Arg Leu Asp
1               5                   10                  15

<210> SEQ ID NO 265
<211> LENGTH: 15
<212> TYPE: PRT
<213> ORGANISM: Helicobacter pylori

<400> SEQUENCE: 265

Thr Gln Val Ala Lys Lys Val Thr Lys Lys Ile Asp Gln Leu Asn
1               5                   10                  15

<210> SEQ ID NO 266
<211> LENGTH: 15
<212> TYPE: PRT
<213> ORGANISM: Helicobacter pylori

<400> SEQUENCE: 266

Arg His Asp Lys Val Asp Asp Leu Ser Lys Ile Gly Arg Ser Val
1               5                   10                  15

<210> SEQ ID NO 267
<211> LENGTH: 15
<212> TYPE: PRT
<213> ORGANISM: Helicobacter pylori

<400> SEQUENCE: 267

Arg His Asp Lys Val Asp Asp Leu Ser Lys Val Gly Leu Ser Arg
1               5                   10                  15
```

<210> SEQ ID NO 268
<211> LENGTH: 15
<212> TYPE: PRT
<213> ORGANISM: Helicobacter pylori

<400> SEQUENCE: 268

Lys His Ala Lys Val Asp Asp Leu Ser Lys Val Gly Arg Ser Val
1               5                   10                  15

<210> SEQ ID NO 269
<211> LENGTH: 15
<212> TYPE: PRT
<213> ORGANISM: Helicobacter pylori

<400> SEQUENCE: 269

Arg His Asp Lys Val Asp Asp Leu Ser Lys Val Gly Leu Ser Ala
1               5                   10                  15

<210> SEQ ID NO 270
<211> LENGTH: 15
<212> TYPE: PRT
<213> ORGANISM: Helicobacter pylori

<400> SEQUENCE: 270

Leu Lys Arg Tyr Ala Lys Val Asp Asp Leu Ser Lys Val Gly Leu
1               5                   10                  15

<210> SEQ ID NO 271
<211> LENGTH: 15
<212> TYPE: PRT
<213> ORGANISM: Helicobacter pylori

<400> SEQUENCE: 271

Arg His Asp Lys Val Asp Asp Leu Ser Lys Val Gly Arg Ser Arg
1               5                   10                  15

<210> SEQ ID NO 272
<211> LENGTH: 15
<212> TYPE: PRT
<213> ORGANISM: Helicobacter pylori

<400> SEQUENCE: 272

Leu Lys Arg Tyr Ala Lys Val Asp Asp Leu Ser Lys Ala Gly Arg
1               5                   10                  15

<210> SEQ ID NO 273
<211> LENGTH: 15
<212> TYPE: PRT
<213> ORGANISM: Helicobacter pylori

<400> SEQUENCE: 273

Arg Tyr Ala Lys Val Asp Asp Leu Ser Lys Val Gly Leu Ser Arg
1               5                   10                  15

<210> SEQ ID NO 274
<211> LENGTH: 15
<212> TYPE: PRT
<213> ORGANISM: Helicobacter pylori

<400> SEQUENCE: 274

Lys Val Asp Asp Leu Ser Lys Val Gly Leu Ser Ala Asn His Glu
1               5                   10                  15

-continued

```
<210> SEQ ID NO 275
<211> LENGTH: 15
<212> TYPE: PRT
<213> ORGANISM: Helicobacter pylori

<400> SEQUENCE: 275

Lys Val Asp Asp Leu Ser Lys Val Gly Leu Ser Arg Glu Gln Glu
1               5                   10                  15

<210> SEQ ID NO 276
<211> LENGTH: 15
<212> TYPE: PRT
<213> ORGANISM: Helicobacter pylori

<400> SEQUENCE: 276

Lys Val Asp Asp Leu Thr Lys Val Gly Phe Ser Arg Glu Gln Glu
1               5                   10                  15

<210> SEQ ID NO 277
<211> LENGTH: 15
<212> TYPE: PRT
<213> ORGANISM: Helicobacter pylori

<400> SEQUENCE: 277

Lys Val Asp Asp Leu Ser Lys Val Gly Leu Ser Ala Asn Pro Glu
1               5                   10                  15

<210> SEQ ID NO 278
<211> LENGTH: 15
<212> TYPE: PRT
<213> ORGANISM: Helicobacter pylori

<400> SEQUENCE: 278

Val Gly Gln Ala Gly Phe Pro Phe Lys Lys His Ala Lys Val Glu
1               5                   10                  15

<210> SEQ ID NO 279
<211> LENGTH: 15
<212> TYPE: PRT
<213> ORGANISM: Helicobacter pylori

<400> SEQUENCE: 279

Gly Ser Ser Pro Leu Lys Arg Tyr Ala Lys Val Asp Asp Leu Ser
1               5                   10                  15

<210> SEQ ID NO 280
<211> LENGTH: 15
<212> TYPE: PRT
<213> ORGANISM: Helicobacter pylori

<400> SEQUENCE: 280

Pro Glu Pro Ile Tyr Ala Thr Ile Asp Phe Asp Ala Asn Gln
1               5                   10                  15

<210> SEQ ID NO 281
<211> LENGTH: 15
<212> TYPE: PRT
<213> ORGANISM: Helicobacter pylori

<400> SEQUENCE: 281

Pro Glu Pro Ile Tyr Ala Thr Ile Asp Phe Asp Glu Ala Asn Gln
1               5                   10                  15

<210> SEQ ID NO 282
<211> LENGTH: 15
```

```
<212> TYPE: PRT
<213> ORGANISM: Helicobacter pylori

<400> SEQUENCE: 282

Ala Val Ser Glu Ala Lys Ala Gly Phe Phe Gly Asn Leu Glu Gln
1               5                   10                  15

<210> SEQ ID NO 283
<211> LENGTH: 15
<212> TYPE: PRT
<213> ORGANISM: Helicobacter pylori

<400> SEQUENCE: 283

Lys Ala Gly Phe Phe Gly Asn Leu Glu Gln Thr Ile Asp Lys Leu
1               5                   10                  15

<210> SEQ ID NO 284
<211> LENGTH: 15
<212> TYPE: PRT
<213> ORGANISM: Helicobacter pylori

<400> SEQUENCE: 284

Ala Val Ser Glu Ala Lys Ala Gly Phe Phe Gly Asn Leu Glu Arg
1               5                   10                  15

<210> SEQ ID NO 285
<211> LENGTH: 15
<212> TYPE: PRT
<213> ORGANISM: Helicobacter pylori

<400> SEQUENCE: 285

Lys Ala Gly Phe Phe Gly Asn Leu Glu Gln Thr Ile Gly Asn Leu
1               5                   10                  15

<210> SEQ ID NO 286
<211> LENGTH: 15
<212> TYPE: PRT
<213> ORGANISM: Helicobacter pylori

<400> SEQUENCE: 286

Lys Val Gly Phe Phe Gly Asn Leu Glu Gln Thr Ile Asp Lys Leu
1               5                   10                  15

<210> SEQ ID NO 287
<211> LENGTH: 15
<212> TYPE: PRT
<213> ORGANISM: Helicobacter pylori

<400> SEQUENCE: 287

Ala Val Ser Glu Ala Lys Val Gly Phe Phe Gly Asn Leu Glu Gln
1               5                   10                  15

<210> SEQ ID NO 288
<211> LENGTH: 15
<212> TYPE: PRT
<213> ORGANISM: Helicobacter pylori

<400> SEQUENCE: 288

Lys Ala Gly Phe Phe Gly Asn Leu Glu Gln Thr Ile Asp Asn Leu
1               5                   10                  15

<210> SEQ ID NO 289
<211> LENGTH: 15
<212> TYPE: PRT
<213> ORGANISM: Helicobacter pylori
```

<400> SEQUENCE: 289

Lys Ala Gly Phe Phe Gly Asn Leu Glu Gln Thr Ile Asn Asn Leu
1               5                   10                  15

<210> SEQ ID NO 290
<211> LENGTH: 15
<212> TYPE: PRT
<213> ORGANISM: Helicobacter pylori

<400> SEQUENCE: 290

Lys Ala Gly Tyr Phe Gly Asn Leu Glu Gln Thr Ile Asp Asn Leu
1               5                   10                  15

<210> SEQ ID NO 291
<211> LENGTH: 15
<212> TYPE: PRT
<213> ORGANISM: Helicobacter pylori

<400> SEQUENCE: 291

Lys Ala Gly Phe Phe Gly Asn Leu Glu Arg Thr Ile Asp Lys Leu
1               5                   10                  15

<210> SEQ ID NO 292
<211> LENGTH: 15
<212> TYPE: PRT
<213> ORGANISM: Helicobacter pylori

<400> SEQUENCE: 292

Ala Val Ser Glu Ala Lys Ser Gly Phe Phe Gly Asn Leu Glu Gln
1               5                   10                  15

<210> SEQ ID NO 293
<211> LENGTH: 15
<212> TYPE: PRT
<213> ORGANISM: Helicobacter pylori

<400> SEQUENCE: 293

Lys Ala Gly Phe Phe Gly Asn Leu Glu Gln Thr Met Asp Arg Leu
1               5                   10                  15

<210> SEQ ID NO 294
<211> LENGTH: 15
<212> TYPE: PRT
<213> ORGANISM: Helicobacter pylori

<400> SEQUENCE: 294

Lys Ala Gly Tyr Phe Gly Asn Leu Glu Gln Thr Ile Asp Lys Leu
1               5                   10                  15

<210> SEQ ID NO 295
<211> LENGTH: 15
<212> TYPE: PRT
<213> ORGANISM: Helicobacter pylori

<400> SEQUENCE: 295

Lys Ala Gly Phe Phe Gly Asn Leu Glu Arg Thr Ile Asp Asn Leu
1               5                   10                  15

<210> SEQ ID NO 296
<211> LENGTH: 15
<212> TYPE: PRT
<213> ORGANISM: Helicobacter pylori

<400> SEQUENCE: 296

Ala Val Ser Glu Ala Lys Ala Gly Tyr Phe Gly Asn Leu Glu Gln
1               5                   10                  15

<210> SEQ ID NO 297
<211> LENGTH: 15
<212> TYPE: PRT
<213> ORGANISM: Helicobacter pylori

<400> SEQUENCE: 297

Lys Val Pro Asp Ser Leu Ser Ala Lys Leu Asp Asn Tyr Ala Thr
1               5                   10                  15

<210> SEQ ID NO 298
<211> LENGTH: 15
<212> TYPE: PRT
<213> ORGANISM: Helicobacter pylori

<400> SEQUENCE: 298

Met Asn Leu Trp Ala Glu Ser Ala Lys Lys Val Pro Ala Gly Leu
1               5                   10                  15

<210> SEQ ID NO 299
<211> LENGTH: 15
<212> TYPE: PRT
<213> ORGANISM: Helicobacter pylori

<400> SEQUENCE: 299

Val Asn Leu Trp Ala Glu Ser Ala Lys Lys Val Pro Val Ser Leu
1               5                   10                  15

<210> SEQ ID NO 300
<211> LENGTH: 15
<212> TYPE: PRT
<213> ORGANISM: Helicobacter pylori

<400> SEQUENCE: 300

Lys Val Pro Ala Ser Leu Leu Glu Lys Leu Asp Asn Tyr Ala Thr
1               5                   10                  15

<210> SEQ ID NO 301
<211> LENGTH: 15
<212> TYPE: PRT
<213> ORGANISM: Helicobacter pylori

<400> SEQUENCE: 301

Met Asn Leu Trp Ala Glu Ser Ala Lys Lys Val Pro Ala Ser Leu
1               5                   10                  15

<210> SEQ ID NO 302
<211> LENGTH: 15
<212> TYPE: PRT
<213> ORGANISM: Helicobacter pylori

<400> SEQUENCE: 302

Val Asn Leu Trp Ala Glu Asn Ala Lys Lys Leu Pro Ala Ser Leu
1               5                   10                  15

<210> SEQ ID NO 303
<211> LENGTH: 15
<212> TYPE: PRT
<213> ORGANISM: Helicobacter pylori

<400> SEQUENCE: 303

Val Glu Ser Ala Lys Gln Val Pro Ala Gly Leu Gln Ala Lys Leu

<210> SEQ ID NO 304
<211> LENGTH: 15
<212> TYPE: PRT
<213> ORGANISM: Helicobacter pylori

<400> SEQUENCE: 304

Asn Gly Gly Ile Asn Glu Lys Ala Thr Gly Met Leu Thr Gln Lys
1               5                   10                  15

<210> SEQ ID NO 305
<211> LENGTH: 15
<212> TYPE: PRT
<213> ORGANISM: Helicobacter pylori

<400> SEQUENCE: 305

Glu Lys Ala Ile Gly Met Leu Thr Gln Lys Asn Pro Glu Trp Leu
1               5                   10                  15

<210> SEQ ID NO 306
<211> LENGTH: 15
<212> TYPE: PRT
<213> ORGANISM: Helicobacter pylori

<400> SEQUENCE: 306

Glu Lys Ala Thr Gly Val Leu Thr Gln Lys Asn Pro Glu Trp Leu
1               5                   10                  15

<210> SEQ ID NO 307
<211> LENGTH: 15
<212> TYPE: PRT
<213> ORGANISM: Helicobacter pylori

<400> SEQUENCE: 307

Glu Lys Ala Thr Gly Met Leu Met Gln Lys Asn Pro Glu Trp Leu
1               5                   10                  15

<210> SEQ ID NO 308
<211> LENGTH: 15
<212> TYPE: PRT
<213> ORGANISM: Helicobacter pylori

<400> SEQUENCE: 308

Lys Asp Tyr Ser Asp Ser Phe Lys Phe Ser Thr Lys Leu Asn Ser
1               5                   10                  15

<210> SEQ ID NO 309
<211> LENGTH: 15
<212> TYPE: PRT
<213> ORGANISM: Helicobacter pylori

<400> SEQUENCE: 309

Gly Ser Val Pro Leu Ser Ala Tyr Asp Lys Ile Gly Phe Asn Gln
1               5                   10                  15

<210> SEQ ID NO 310
<211> LENGTH: 15
<212> TYPE: PRT
<213> ORGANISM: Helicobacter pylori

<400> SEQUENCE: 310

Gly Ser Val Ser Leu Ser Glu Tyr Asp Lys Ile Gly Phe Asn Gln
1               5                   10                  15

<210> SEQ ID NO 311
<211> LENGTH: 15
<212> TYPE: PRT
<213> ORGANISM: Helicobacter pylori

<400> SEQUENCE: 311

Gly Ser Thr His Leu Ser Glu Tyr Asp Lys Ile Gly Phe Asn Gln
1               5                   10                  15

<210> SEQ ID NO 312
<211> LENGTH: 15
<212> TYPE: PRT
<213> ORGANISM: Helicobacter pylori

<400> SEQUENCE: 312

Leu Ser Glu Tyr Asp Asn Ile Gly Phe Ser Gln Lys Asn Met Lys
1               5                   10                  15

<210> SEQ ID NO 313
<211> LENGTH: 15
<212> TYPE: PRT
<213> ORGANISM: Helicobacter pylori

<400> SEQUENCE: 313

Gly Ser Ala His Leu Ser Glu Tyr Asp Lys Ile Gly Phe Asn Gln
1               5                   10                  15

<210> SEQ ID NO 314
<211> LENGTH: 15
<212> TYPE: PRT
<213> ORGANISM: Helicobacter pylori

<400> SEQUENCE: 314

Gly Ser Ala Pro Leu Ser Asp Tyr Asp Lys Ile Gly Phe Asn Gln
1               5                   10                  15

<210> SEQ ID NO 315
<211> LENGTH: 15
<212> TYPE: PRT
<213> ORGANISM: Helicobacter pylori

<400> SEQUENCE: 315

Asp Ser Phe Lys Phe Ser Thr Lys Leu Asn Ser Ala Ile Lys Asp
1               5                   10                  15

<210> SEQ ID NO 316
<211> LENGTH: 15
<212> TYPE: PRT
<213> ORGANISM: Helicobacter pylori

<400> SEQUENCE: 316

Gly Ser Val Pro Leu Ser Glu Tyr Asp Lys Ile Gly Phe Asn Gln
1               5                   10                  15

<210> SEQ ID NO 317
<211> LENGTH: 15
<212> TYPE: PRT
<213> ORGANISM: Helicobacter pylori

<400> SEQUENCE: 317

Gly Ser Ala Pro Leu Ser Glu Tyr Asp Asn Ile Gly Phe Ser Gln
1               5                   10                  15

<210> SEQ ID NO 318

```
<210> SEQ ID NO 318
<211> LENGTH: 15
<212> TYPE: PRT
<213> ORGANISM: Helicobacter pylori

<400> SEQUENCE: 318

Gly Ser Ala Pro Leu Ser Glu Tyr Asp Lys Ile Gly Phe Asn Gln
1               5                   10                  15

<210> SEQ ID NO 319
<211> LENGTH: 15
<212> TYPE: PRT
<213> ORGANISM: Helicobacter pylori

<400> SEQUENCE: 319

Gly Ser Ala Pro Leu Ser Ala Tyr Asp Lys Ile Gly Phe Asn Gln
1               5                   10                  15

<210> SEQ ID NO 320
<211> LENGTH: 15
<212> TYPE: PRT
<213> ORGANISM: Helicobacter pylori

<400> SEQUENCE: 320

Asp Ser Phe Lys Phe Ser Thr Lys Leu Asn Asp Ala Val Lys Asp
1               5                   10                  15

<210> SEQ ID NO 321
<211> LENGTH: 15
<212> TYPE: PRT
<213> ORGANISM: Helicobacter pylori

<400> SEQUENCE: 321

Asp Ser Phe Lys Phe Ser Thr Lys Leu Asn Asn Ala Val Lys Asn
1               5                   10                  15

<210> SEQ ID NO 322
<211> LENGTH: 15
<212> TYPE: PRT
<213> ORGANISM: Helicobacter pylori

<400> SEQUENCE: 322

Gly Ser Val Pro Leu Ser Glu Tyr Asp Asn Ile Gly Phe Asn Gln
1               5                   10                  15

<210> SEQ ID NO 323
<211> LENGTH: 15
<212> TYPE: PRT
<213> ORGANISM: Helicobacter pylori

<400> SEQUENCE: 323

Asp Ser Phe Lys Phe Ser Thr Lys Leu Asn Asn Ala Val Lys Asp
1               5                   10                  15

<210> SEQ ID NO 324
<211> LENGTH: 15
<212> TYPE: PRT
<213> ORGANISM: Helicobacter pylori

<400> SEQUENCE: 324

Asp Ser Phe Lys Phe Ser Thr Lys Leu Ser Asn Ala Val Lys Asn
1               5                   10                  15

<210> SEQ ID NO 325
<211> LENGTH: 15
<212> TYPE: PRT
```

-continued

```
<213> ORGANISM: Helicobacter pylori

<400> SEQUENCE: 325

Asp Ser Phe Lys Phe Ser Thr Arg Leu Asn Asn Ala Val Lys Asp
1               5                   10                  15

<210> SEQ ID NO 326
<211> LENGTH: 15
<212> TYPE: PRT
<213> ORGANISM: Helicobacter pylori

<400> SEQUENCE: 326

Gly Ser Thr Pro Leu Ser Asp Tyr Asp Lys Ile Gly Phe Asn Gln
1               5                   10                  15

<210> SEQ ID NO 327
<211> LENGTH: 15
<212> TYPE: PRT
<213> ORGANISM: Helicobacter pylori

<400> SEQUENCE: 327

Asp Ser Phe Lys Phe Ser Thr Glu Leu Asn Asn Ala Val Lys Asp
1               5                   10                  15

<210> SEQ ID NO 328
<211> LENGTH: 15
<212> TYPE: PRT
<213> ORGANISM: Helicobacter pylori

<400> SEQUENCE: 328

Gly Ser Thr Pro Leu Ser Glu Tyr Asp Lys Ile Gly Phe Asn Gln
1               5                   10                  15

<210> SEQ ID NO 329
<211> LENGTH: 15
<212> TYPE: PRT
<213> ORGANISM: Helicobacter pylori

<400> SEQUENCE: 329

Asp Ser Phe Lys Phe Ser Thr Lys Leu Ser Asn Ala Val Lys Asp
1               5                   10                  15

<210> SEQ ID NO 330
<211> LENGTH: 15
<212> TYPE: PRT
<213> ORGANISM: Helicobacter pylori

<400> SEQUENCE: 330

Asp Ser Phe Lys Phe Ser Thr Lys Ser Asn Asn Ala Val Lys Asp
1               5                   10                  15

<210> SEQ ID NO 331
<211> LENGTH: 17
<212> TYPE: PRT
<213> ORGANISM: Artificial Sequence
<220> FEATURE:
<223> OTHER INFORMATION: Biotin tag
<220> FEATURE:
<221> NAME/KEY: MISC_FEATURE
<222> LOCATION: (2)..(16)
<223> OTHER INFORMATION: Xaa is any amino acid
```

```
<400> SEQUENCE: 331

His Xaa Xaa Xaa Xaa Xaa Xaa Xaa Xaa Xaa Xaa Xaa Xaa Xaa Xaa Xaa
1               5                   10                  15

Lys

<210> SEQ ID NO 332
<211> LENGTH: 5
<212> TYPE: PRT
<213> ORGANISM: Helicobacter pylori

<400> SEQUENCE: 332

Glu Pro Ile Tyr Ala
1               5
```